United States Patent
McClymont et al.

(10) Patent No.: US 12,171,419 B2
(45) Date of Patent: Dec. 24, 2024

(54) OFFSET HOHMANN

(71) Applicant: K2M, Inc., Leesburg, VA (US)

(72) Inventors: Kaitlin Elizabeth Anne McClymont, Reston, VA (US); Nicholas Padovani, Fairfax, VA (US); Pauline Patricia Hutton, Gainesville, VA (US); Alexander Horia Artaki, Washington, DC (US)

(73) Assignee: K2M, Inc., Leesburg, VA (US)

( * ) Notice: Subject to any disclaimer, the term of this patent is extended or adjusted under 35 U.S.C. 154(b) by 14 days.

(21) Appl. No.: 17/960,427

(22) Filed: Oct. 5, 2022

(65) Prior Publication Data

US 2023/0103459 A1 Apr. 6, 2023

Related U.S. Application Data

(60) Provisional application No. 63/252,797, filed on Oct. 6, 2021.

(51) Int. Cl.
*A61B 17/02* (2006.01)
*A61B 17/00* (2006.01)

(52) U.S. Cl.
CPC ...... *A61B 17/02* (2013.01); *A61B 2017/0042* (2013.01)

(58) Field of Classification Search
CPC .. A61B 17/02; A61B 17/0206; A61B 17/0218
See application file for complete search history.

(56) References Cited

U.S. PATENT DOCUMENTS

| 3,467,079 A | 9/1969 | Charles |
| 3,731,673 A | 5/1973 | Halloran |
| 4,562,832 A | 1/1986 | Wilder et al. |

(Continued)

FOREIGN PATENT DOCUMENTS

| AU | 2013205982 A1 | 12/2013 |
| KR | 20150012545 A | 2/2015 |

(Continued)

OTHER PUBLICATIONS

OLIF Procedures—OLIF51 Products, Medtronic, web page https://www.medtronic.com/us-en/healthcare-professionals/therapies-procedures/spinal-orthopaedic/olif/products/olif51.html, pp. 1-11, Mar. 2021, retrieved from https://www.medtronic.com/us-en/healthcare professionals/therapies-procedures/spinal-orthopaedic/olif/products/olif51.html on Aug. 26, 2021.

(Continued)

*Primary Examiner* — Julianna N Harvey
*Assistant Examiner* — Anna V. Little
(74) *Attorney, Agent, or Firm* — Lerner David LLP

(57) ABSTRACT

A surgical retractor tool includes a handle and a blade extending transversely from a front end of the handle. The blade includes a proximal portion and a distal portion with respective proximal and distal tissue engaging surfaces. The distal tissue engaging surface may be skewed relative to the proximal tissue engaging surface such that the handle may be angled relative to a direction of retraction when the surgical retractor tool is used. A distal tip of the retractor may include a curved tongue that may be curved in a direction opposite the direction of retraction.

16 Claims, 11 Drawing Sheets

(56) References Cited

U.S. PATENT DOCUMENTS

| | | | |
|---|---|---|---|
| 5,514,075 A * | 5/1996 | Moll | A61B 90/50 606/198 |
| 6,116,580 A | 9/2000 | Hull | |
| 6,322,499 B1 | 11/2001 | Evans et al. | |
| 6,464,634 B1 * | 10/2002 | Fraser | A61B 17/0293 600/233 |
| 6,739,744 B2 | 5/2004 | Williams | |
| 7,022,069 B1 | 4/2006 | Masson et al. | |
| 7,150,714 B2 | 12/2006 | Myles | |
| 7,223,233 B2 | 5/2007 | Branch et al. | |
| 7,326,216 B2 | 2/2008 | Bertagnoli et al. | |
| 7,491,168 B2 | 2/2009 | Raymond et al. | |
| 7,686,492 B2 | 3/2010 | Vayser et al. | |
| 7,874,982 B2 | 1/2011 | Selover et al. | |
| 8,088,066 B2 | 1/2012 | Grey | |
| 8,317,693 B2 | 11/2012 | Grey et al. | |
| 8,454,621 B2 | 6/2013 | DeRidder et al. | |
| 8,556,485 B2 | 10/2013 | Geuder | |
| 8,647,333 B2 | 2/2014 | Mansour | |
| 8,727,975 B1 | 5/2014 | Pfabe et al. | |
| 8,936,551 B2 | 1/2015 | Vayser | |
| 9,011,323 B2 | 4/2015 | Vayser | |
| 9,044,280 B1 | 6/2015 | Arambula et al. | |
| 9,107,649 B2 | 8/2015 | Frey | |
| 9,113,853 B1 | 8/2015 | Casey et al. | |
| 9,125,587 B2 | 9/2015 | Hawkins et al. | |
| 9,408,598 B1 | 8/2016 | Fantini et al. | |
| 9,554,867 B2 | 1/2017 | Cosmescu | |
| 9,622,779 B2 | 4/2017 | Horton | |
| 9,718,130 B1 | 8/2017 | Vayser | |
| 9,956,053 B2 | 5/2018 | Diao | |
| 9,999,345 B2 | 6/2018 | Vayser | |
| 10,045,768 B2 | 8/2018 | Garcia-Bengochea | |
| 10,098,622 B2 | 10/2018 | Seex | |
| 10,307,290 B2 | 6/2019 | Kern | |
| 10,420,540 B2 | 9/2019 | Swift | |
| 10,463,444 B2 | 11/2019 | Davis | |
| D875,928 S | 2/2020 | Zagatsky | |
| 10,548,645 B2 | 2/2020 | Lowry | |
| 10,806,537 B2 | 10/2020 | Mark | |
| 10,881,387 B2 | 1/2021 | Swift | |
| 10,952,712 B2 | 3/2021 | Swift | |
| 10,993,739 B2 | 5/2021 | Solitario, Jr. | |
| 11,191,533 B2 | 12/2021 | Seex | |
| 11,197,662 B2 | 12/2021 | Swift | |
| 11,382,711 B2 | 7/2022 | Grey | |
| 11,439,379 B2 | 9/2022 | Swift | |
| 11,529,131 B1 | 12/2022 | Chambers et al. | |
| 2002/0058931 A1 | 5/2002 | Parker | |
| 2005/0085699 A1 | 4/2005 | Weiss | |
| 2005/0228233 A1 * | 10/2005 | Ritland | A61B 17/025 600/210 |
| 2006/0052671 A1 * | 3/2006 | McCarthy | A61B 17/0206 600/232 |
| 2007/0060795 A1 | 3/2007 | Vayser et al. | |
| 2007/0083086 A1 * | 4/2007 | LeVahn | A61B 17/02 600/210 |
| 2008/0039870 A1 | 2/2008 | Golta | |
| 2008/0058606 A1 | 3/2008 | Miles et al. | |
| 2009/0036746 A1 | 2/2009 | Blackwell et al. | |
| 2009/0203969 A1 | 8/2009 | Cohen et al. | |
| 2011/0270042 A1 | 11/2011 | Giulianotti | |
| 2012/0271120 A1 * | 10/2012 | Seex | A61B 17/02 600/235 |
| 2013/0102850 A1 * | 4/2013 | Fiorella | A61B 1/04 600/210 |
| 2013/0231538 A1 * | 9/2013 | Guilford | A61B 17/02 600/210 |
| 2014/0039267 A1 | 2/2014 | Seex et al. | |
| 2014/0135584 A1 | 5/2014 | Lee et al. | |
| 2014/0236300 A1 | 8/2014 | Lowry | |
| 2014/0257035 A1 | 9/2014 | Blain | |
| 2014/0275801 A1 * | 9/2014 | Menchaca | A61B 17/0293 600/212 |
| 2014/0323811 A1 | 10/2014 | DeSantis et al. | |
| 2015/0018623 A1 | 1/2015 | Friedrich et al. | |
| 2015/0018628 A1 | 1/2015 | Friedrich et al. | |
| 2015/0150693 A1 | 6/2015 | Gharib et al. | |
| 2015/0173733 A1 | 6/2015 | Ryshkus et al. | |
| 2015/0196196 A1 | 7/2015 | Vayser | |
| 2015/0216517 A1 | 8/2015 | Bjork et al. | |
| 2015/0297247 A1 | 10/2015 | Seex | |
| 2015/0305731 A1 | 10/2015 | Friedrich et al. | |
| 2015/0366549 A1 | 12/2015 | Cao et al. | |
| 2016/0106408 A1 | 4/2016 | Ponmudi et al. | |
| 2016/0192922 A1 | 7/2016 | Friedrich et al. | |
| 2016/0270773 A1 * | 9/2016 | Bailey | A61B 1/32 |
| 2016/0287236 A1 * | 10/2016 | Garcia-Bengochea | A61B 17/0218 |
| 2017/0003540 A1 | 1/2017 | Chen et al. | |
| 2017/0035404 A1 | 2/2017 | Foster | |
| 2017/0042524 A1 | 2/2017 | Angus et al. | |
| 2017/0224324 A1 | 8/2017 | Horton | |
| 2017/0296160 A1 | 10/2017 | O'Brien | |
| 2017/0303905 A1 | 10/2017 | Wilson | |
| 2017/0311940 A1 * | 11/2017 | Daavettila | A61B 17/0206 |
| 2018/0177525 A1 | 6/2018 | Gan | |
| 2018/0303473 A1 | 10/2018 | Spann et al. | |
| 2018/0344375 A1 | 12/2018 | Seavey et al. | |
| 2019/0021716 A1 | 1/2019 | Waugh et al. | |
| 2019/0076138 A1 | 3/2019 | Opperman | |
| 2019/0350571 A1 | 11/2019 | Swift | |
| 2020/0015799 A1 * | 1/2020 | Tsubouchi | A61B 17/0206 |
| 2020/0038063 A1 | 2/2020 | Choi et al. | |
| 2020/0046336 A1 | 2/2020 | Swift et al. | |
| 2020/0121305 A1 | 4/2020 | Komsa | |
| 2020/0129168 A1 | 4/2020 | Reitblat | |
| 2020/0138542 A1 | 5/2020 | Shafer-Zatko | |
| 2020/0138543 A1 | 5/2020 | Marsh | |
| 2020/0214686 A1 | 7/2020 | Truckey et al. | |
| 2020/0237204 A1 | 7/2020 | Molnar | |
| 2020/0367874 A1 | 11/2020 | Huang | |
| 2020/0367875 A1 | 11/2020 | Nowak et al. | |
| 2021/0052346 A1 | 2/2021 | Stanley | |
| 2021/0259674 A1 | 8/2021 | Swift | |
| 2021/0315563 A1 | 10/2021 | Williams et al. | |
| 2022/0117592 A1 | 4/2022 | James et al. | |
| 2022/0175362 A1 | 6/2022 | Considine et al. | |
| 2022/0401094 A1 | 12/2022 | Zagatsky et al. | |

FOREIGN PATENT DOCUMENTS

| | | | |
|---|---|---|---|
| WO | 2005048855 A1 | 6/2005 | |
| WO | 2011087462 A1 | 7/2011 | |
| WO | 2017175024 A2 | 10/2017 | |
| WO | 2017213662 A1 | 12/2017 | |
| WO | WO-2020058644 A1 * | 3/2020 | A61B 17/025 |
| WO | 2021102474 A2 | 5/2021 | |

OTHER PUBLICATIONS

Extended European Search Report issued in Appln. No. 22199903.0 mailed Mar. 3, 2023 (6 pages).

* cited by examiner

OFFSET HOHMANN

CROSS-REFERENCE TO RELATED APPLICATION

The present application claims the benefit of the filing date of U.S. Provisional Patent Application No. 63/252,797, filed Oct. 6, 2021, the disclosure of which is hereby incorporated by reference herein in its entirety.

BACKGROUND

Many surgical procedures require access to regions deep within a patient or to access spaces, such as interiors of joints, between two or more tightly situated bones. To gain and maintain access to the target regions within a patient, it is common to pull back overlying tissues while a surgical procedure is performed. A variety of tools are available for this purpose. Some examples of such tools are Hohmann blades. Hohmann blades are typically flat or slightly curved and may include a handle often configured for manual use. Hohmann blades occasionally have mechanical attachment points for connection to mechanical retractor assemblies or surgical robots in addition to or instead of manually operated handles.

Hohmann blades for both manual and mechanical use are usually configured to retract tissue in one direction relative to the tool overall. Specifically, known Hohmann blades are constructed to pull tissue along an axis that either intersects or is parallel to an axis along which the handle extends. However, the nature of some surgical procedures, such as those involving access to the spine, particular directions of access to a surgical site, individual anatomies, surgeon preference, and construction of mechanical assemblies or surgical robots limit the efficiency and effectiveness of known Hohmann blades, thereby making surgery more difficult and cumbersome. Improvements in Hohmann blade designs would therefore be beneficial.

BRIEF SUMMARY

According to some aspects, a retractor may include a handle extending along a handle axis and a blade connected to and extending from the handle. At least a proximal portion of the blade may extend along a proximal blade axis. The handle axis may be parallel to or may intersect a front-to-back axis. A distal portion of the blade may have a tissue engaging surface that extends along a distal blade plane that faces obliquely and is laterally offset relative to the handle axis. In such an arrangement, lateral refers to a direction that is transverse to both the proximal blade axis and the front-to-back axis. The distal portion of the blade may have a front surface that is not parallel to the front surface of the proximal portion of the blade. The front surface of the distal portion of the blade may be skewed laterally relative to the front surface of the proximal portion of the blade such that the front surface of the distal portion is twisted relative to the front surface of the proximal portion. In addition to or in the alternative to the above, the distal portion of the blade may be laterally offset from the proximal portion of the blade. The distal blade plane may include the proximal blade axis or extend parallel to the proximal blade axis.

A back lip curling generally backward relative to handle may define a distal end of the blade. The back lip may hook or point toward a hook direction defined by an orientation of a sharp end of the back lip that corresponds to a direction of travel along which the back lip and the retractor overall will most effectively engage tissue. The hook direction may be laterally transverse to the handle axis.

In another aspect, a surgical retractor tool may comprise a handle extending along a first axis and a blade extending vertically from a front end of the handle. The blade may comprise a tissue engaging surface at a distal end thereof that is skewed laterally relative to the first axis.

In some arrangements according to any of the foregoing, the blade may comprise a proximal portion extending along a second axis that is transverse to the first axis. The blade may also comprise a distal portion that defines the tissue engaging surface such that the tissue engaging surface extends on a distal blade plane that either includes the second axis or is parallel to the second axis. A smallest angle between the first axis and the second axis may be greater than a smallest angle between the first axis and the plane.

In some arrangements according to any of the foregoing, the distal portion of the blade may be wider than the proximal portion of the blade.

In some arrangements according to any of the foregoing, the distal blade plane may be normal to axes having a lateral component and the first axis has no lateral component.

In some arrangements according to any of the foregoing, the distal blade plane may be offset from the proximal blade axis.

In some arrangements according to any of the foregoing, the tissue engaging surface may be offset laterally from a location at which the blade meets the handle.

In some arrangements according to any of the foregoing, the tool may comprise a back lip defining a distal end of the blade. The back lip may be pointed in a hook direction that is laterally transverse to the first axis.

In some arrangements according to any of the foregoing, the back lip may be laterally offset from the first axis.

In some arrangements according to any of the foregoing, the hook direction may be along an axis that neither intersects nor extends parallel to the first axis.

In some arrangements according to any of the foregoing, the hook direction may be laterally aligned with a tissue engaging surface defined by a distal portion of the blade.

In some arrangements according to any of the foregoing, the tissue engaging portion may extend along a distal blade plane that is vertical and transverse to the first axis by an angle that is smaller than a smallest angle between the first axis and a second axis along which a proximal portion of the blade extends.

In another aspect, a surgical retractor tool may comprise a handle extending along a first axis. The tool may also comprise a blade extending vertically from the handle. The blade may comprise a back lip at a distal end of the blade, the back lip pointing along a hook direction that is laterally transverse to the first axis.

In some arrangements according to any of the foregoing, the hook direction may be along an axis that does not intersect the handle axis.

In some arrangements according to any of the foregoing, the blade may comprise a proximal portion extending along a vertical second axis. A distal portion may have a tissue engaging surface adjacent to the back lip, the tissue engaging surface extending along a distal blade plane with which the hook direction is laterally aligned.

In some arrangements according to any of the foregoing, the distal blade plane may be vertical.

In some arrangements according to any of the foregoing, the distal portion of the blade may be laterally offset from the handle axis.

In some arrangements according to any of the foregoing, a smallest angle between the first axis and the second axis may be greater than a smallest angle between the distal blade plane and the handle axis.

In another aspect, a surgical retractor tool may comprise a handle extending along a first axis. The tool may also comprise a blade extending from the handle and including a distal portion having defining a tissue engaging surface that extends along a distal blade plane. No plane may exist that contains both the first axis and any axis normal to the distal blade plane.

In some arrangements according to any of the foregoing, the tool may comprise a back lip defining a distal end of the distal portion. The back lip may be pointed in a hook direction along a second axis, wherein no plane exists that contains both the first axis and the second axis.

In some arrangements according to any of the foregoing, the tool may comprise a proximal portion of the blade that extends in a vertical direction between the handle and the distal portion, and wherein the tissue engaging surface is offset horizontally from the proximal portion.

In some arrangements according to any of the foregoing, the tissue engaging surface may be offset horizontally from the proximal portion along a direction contained by the distal blade plane.

In another aspect, a surgical retractor tool may comprise a handle adapted for holding the retractor tool. The tool may also comprise a blade extending from a front end of the handle at a non-zero angle relative to the handle, the blade comprising a proximal portion and a distal portion, a first front surface extending across a width of the distal portion being skewed relative to a second front surface extending across a width of the proximal portion.

In some arrangements according to any of the foregoing, the second front surface of the proximal portion may pass through a first plane and the first front surface of the distal portion passes through a second plane, the second plane crossing the first plane along an axis through a length of the blade.

In some arrangements according to any of the foregoing, the distal portion may have a first central longitudinal axis and the proximal portion has a second central longitudinal axis, the first central longitudinal axis being laterally offset from the second central longitudinal axis.

In some arrangements according to any of the foregoing, the handle may extend along a first axis and the proximal portion extends along a second axis that is transverse to the first axis, the second axis passing through the distal portion.

In some arrangements according to any of the foregoing, the first front surface of the distal portion may extend along a distal blade plane, the second axis being parallel to the distal blade plane and wherein a smallest true angle between the first axis and the second axis is greater than a smallest true angle between the first axis and the distal blade plane.

In some arrangements according to any of the foregoing, the distal portion of the blade may be wider than the proximal portion of the blade.

In some arrangements according to any of the foregoing, the first axis may not be normal to the distal blade plane from a perspective along the second axis.

In some arrangements according to any of the foregoing, the second axis may not pass through the distal blade plane.

In some arrangements according to any of the foregoing, a tissue engaging surface of the distal portion may be spaced apart from the front end of the handle.

In some arrangements according to any of the foregoing, the tool may comprise a distal end with a tapered tip curving out of the distal blade plane such that the tapered tip and the handle extend from the same side of the distal blade plane.

In some arrangements according to any of the foregoing, the tip may be laterally offset from a plane through the proximal portion and the handle.

In some arrangements according to any of the foregoing, the tip may curve out in a direction along an axis that neither intersects nor extends parallel to the first axis.

In some arrangements according to any of the foregoing, the tip may be laterally aligned with a tissue engaging surface defined by a distal portion of the blade.

In some arrangements according to any of the foregoing, the distal blade plane may be transverse to the first axis by an angle that is smaller than a smallest angle between the proximal blade plane and the first axis, the first axis coincident with a central elongate axis of the handle.

In some arrangements according to any of the foregoing, the tool may comprise a channel extending along a center of the first front surface.

In some arrangements according to any of the foregoing, the channel may extend in a direction that is perpendicular to the width of the distal portion.

In some arrangements according to any of the foregoing, the distal portion may be skewed by 25 to 35 degrees from the proximal portion such that an angle between the first front surface and the second front surface is in a range from 25 to 35 degrees.

In some arrangements according to any of the foregoing, the handle may be centered along a first axis normal to the first plane when viewed in a plane perpendicular to both the first and second planes.

In some arrangements according to any of the foregoing, the handle may be centered along a first axis at an acute or obtuse angle relative to the first plane when viewed in a plane perpendicular to both the first and second planes.

In some arrangements according to any of the foregoing, an angle between the first front surface and the second front surface may be in a range from 25 to 35 degrees.

In some arrangements according to any of the foregoing, the handle may have a first part adjacent to the proximal portion of the blade and a second part extending from the first part to a free end, a length encompassing the first and second parts being non-linear.

In some arrangements according to any of the foregoing, a distal tip of the distal portion may be a tongue extending in a direction that is normal to a width direction of the distal portion, the tongue extending from the distal portion away from the handle.

In yet another aspect, a surgical retractor tool includes a handle and a blade extending from an end of the handle. The blade has a length extending from a proximal end of a proximal portion of the blade to a distal end of a distal portion of the blade, the proximal portion having first and second lateral edges and the distal portion having third and fourth lateral edges. The first and second lateral edges may be coincident with a first plane and the third and fourth lateral edges may be coincident with a second plane, the first plane being transverse to the second plane.

In some arrangements, the second lateral edge and the fourth lateral edge may be coincident with a first linear axis. In other arrangements, the blade may include a tongue that defines a distalmost portion of the distal portion, the tongue curving into a first side of the second plane opposite a second side of the second plane. In arrangements with such a tongue, the handle may be on the second side. In other arrangements, a surface of the tongue facing away from the second side may be concave and a tip of the tongue may be curved. In some arrangements, the distal portion of the blade may partially on and extend from one side of the first plane. In some arrangements, a central longitudinal axis of the handle may be at an angle relative to the first plane. In some arrangements, a minimum distance between the first and second lateral sides may be less than a minimum distance between the third and fourth lateral sides. In some arrangements, the blade may include a transition region between the proximal portion and the distal portion, the transition region having a front surface including a concave surface and a convex surface. The front surface of the transition region may be opposite a tissue contacting surface of the transition region. In some arrangements, the handle may include an elongate slot enclosed within a length of the handle. The elongate slot may extend through an entire depth of the handle and include opposite ends with a wider dimension than a central segment in between the opposite ends. In some arrangements, the distal portion may be skewed relative to the proximal portion such that an angle between the first plane and the second plane is in a range from 5 to 55 degrees.

In another aspect, a surgical retractor tool includes a handle adapted for holding the retractor tool and a blade extending from a front end of the handle at a non-zero angle relative to the handle. The blade may include a proximal portion and a distal portion. A first front surface extending across a width of the distal portion may be skewed relative to a second front surface extending across a width of the proximal portion.

In some arrangements, the second front surface of the proximal portion may pass through a first plane and the first front surface of the distal portion may pass through a second plane, the second plane crossing the first plane along an axis through a length of the blade. In some arrangements, the distal portion may have a first central longitudinal axis and the proximal portion may have a second central longitudinal axis where the first central longitudinal axis may be laterally offset from the second central longitudinal axis. In some arrangements, the distal portion of the blade may be wider than the proximal portion of the blade. In some arrangements, a lateral edge of the blade may flare outward from a distal end of the proximal portion toward the distal portion. In some arrangements, the blade may include a distal end with a tapered tip curving out of the second plane such that the tapered tip and the handle extend from the same side of the second plane. In some arrangements, the blade may include a distal end with a tapered tip curving out of the second plane such that the tapered tip is on a first side of the second plane and the handle is on a second side of the second plane. In some arrangements, the distal portion may be skewed relative to the proximal portion such that an angle between a first plane through lateral sides of the first front surface and a second plane through lateral sides of the second front surface is in a range from 25 to 35 degrees.

In another aspect, a surgical blade may comprise a first elongate part and a second elongate part extending from the first elongate part. The second elongate part may be laterally offset and twisted relative to the first elongate part such that a second central axis through a width of the second elongate part is offset from a first central axis through a width of the first elongate part. A third central axis may pass through the first and second central axes, the third central axis being at an acute angle relative to a width direction of the first elongate part.

In some arrangements according to any of the foregoing, the end of one of the first elongate part and the second elongate part may include a tapered tip bending out of a plane through the one of the first elongate part and the second elongate part.

In some arrangements according to any of the foregoing, the blade may comprise a handle extending from the first elongate part.

In some arrangements according to any of the foregoing, a central longitudinal axis through the handle may be orthogonal to a front surface of the first elongate part.

In some arrangements according to any of the foregoing, the tapered tip may define a hook.

In some arrangements according to any of the foregoing, the first elongate part may be a proximal portion and the second elongate part is a distal portion having tissue engaging surface and a hook shaped tip, the tissue engaging surface extending along a distal blade plane with which the hook shaped tip is laterally aligned.

In some arrangements according to any of the foregoing, the distal portion of the blade may be laterally offset from the handle axis.

In some arrangements according to any of the foregoing, a smallest true angle between the first axis and the second axis may be greater than a smallest true angle between the distal blade plane and the handle axis.

In another aspect, a surgical retractor tool may comprise a handle extending along a first linear axis and a blade extending from the handle, the blade including a proximal portion and a distal portion. The distal portion may define a tissue engaging surface that extends through or approximately parallel to a distal blade plane, wherein the distal blade plane is at an acute or obtuse angle relative to the first linear axis when measured in a plane perpendicular to an elongate dimension of the distal portion.

In some arrangements according to any of the foregoing, the blade may include a distal end defining a back lip, the back lip having a hook shape curved such that both the handle and the back lip are on a first side of the distal blade plane.

In some arrangements according to any of the foregoing, the tissue engaging surface may be laterally offset from the proximal portion.

In some arrangements according to any of the foregoing, the proximal portion may extend along a second linear axis and the tissue engaging surface is offset from the proximal portion along an axis that is perpendicular to the second linear axis contained by the distal blade plane.

In another aspect, a surgical retractor tool may comprise a handle and a blade extending from a front end of the handle. The blade may comprise a proximal portion and a distal portion, a first central longitudinal axis of the distal portion being laterally offset relative to a second central longitudinal axis of the proximal portion. A majority of the proximal portion and a majority of the distal portion may pass through a first plane, the handle extending away from the first plane.

In some arrangements according to any of the foregoing, the proximal portion may define a proximal front surface and the distal portion defines a distal front surface, the distal front surface being transverse to the proximal front surface.

In some arrangements according to any of the foregoing, the proximal front surface and the distal front surface may both be parallel to the first central longitudinal axis and the second central longitudinal axis.

In some arrangements according to any of the foregoing, the first plane may contain an axis that passes through the proximal front surface and the distal front surface.

In some arrangements according to any of the foregoing, the first longitudinal axis, the second longitudinal axis, and a third axis that is normal to both the second longitudinal axis and a central longitudinal axis of the handle may all be contained by a common plane.

In another aspect, a method of retracting tissue during a surgical procedure may comprise contacting tissue with a blade that includes a first surface extending through a first plane. The method may also comprise pulling a handle connected to the blade in a retraction direction that is normal to the first plane and to a point of contact between the tissue and the blade, wherein a central longitudinal axis of the handle does not intersect or extend parallel to the retraction direction.

In some arrangements according to any of the foregoing, the first surface may be a front surface of a distal portion of the blade and the blade further comprises a proximal portion having a front surface that is transverse to the first plane.

In some arrangements according to any of the foregoing, the front surface of the proximal portion may define a second plane that contains an axis parallel to the first plane, and wherein a true acute angle between the central longitudinal axis of the handle and the second plane is greater than a true acute angle between the central longitudinal axis of the handle and the first plane.

In some arrangements according to any of the foregoing, the method may comprise reaching manually or with a tool through a space that is laterally between two lateral edges of a distal portion of the blade that defines the first surface, aligned with the distal portion in the retraction direction, and located at least as deep as the central longitudinal axis of the handle along a depth direction that is normal to both a lateral axis and the retraction direction and parallel to a central longitudinal axis of a proximal portion of the blade, with the point of contact being deeper than the handle.

In some arrangements according to any of the foregoing, the pulling step may pull the tissue out of a cavity and the reaching step includes reaching manually or with a tool into the cavity.

In another aspect, a method of retracting tissue during a surgical procedure may comprise contacting tissue with a distal portion of a blade that includes a proximal portion extending along a proximal blade axis. The method may also comprise pulling a handle connected to the blade in a retraction direction that is normal to a point of contact between the tissue and the blade. The method may also comprise reaching manually or with a tool through a space that is laterally between two lateral edges of the distal portion of the blade, aligned with the distal portion in the retraction direction, and located at least as deep as a central longitudinal axis of the handle along a depth direction that is normal to both a lateral axis and the retraction direction and parallel to a central longitudinal axis of a proximal portion of the blade, with the point of contact being deeper than the handle.

In some arrangements according to any of the foregoing, the pulling step may pull the tissue out of a cavity and the reaching step includes reaching manually or with a tool into the cavity.

In some arrangements according to any of the foregoing, the retraction direction may not intersect or extend parallel to the central longitudinal axis of the handle.

In some arrangements according to any of the foregoing, the distal portion may include a surface that extends along a plane that does not contain any axis that is normal to both the retraction direction and the central longitudinal axis of the handle.

In another aspect, the present disclosure relates to a method of retracting tissue during a surgical procedure by bringing a retractor tool into a surgical field and pulling a handle of the retractor tool to increase the size of an access portal. The method may have steps that include: pressing a first tissue contact surface on a distal portion of a blade of a retractor against tissue of a patient; and pulling a handle extending from the blade in a retraction direction that is normal to a first plane coincident with lateral edges of the blade laterally adjacent to the first tissue contact surface such that tissue is retracted in the retraction direction, wherein the handle is outside of a second plane coincident with a central longitudinal axis of the distal portion and a path of retraction. In this method, the handle may have an elongate dimension transverse to the second plane.

In some arrangements, pulling the handle may include pulling a proximal portion of the blade to retract tissue where the proximal portion of the blade has a second tissue contact surface transverse to the first tissue contact surface.

DETAILED DESCRIPTION

As used herein, the term "distal" refers to that portion of the instrument, or component thereof which is farther from the user while the term "proximal" refers to that portion of the instrument or component thereof which is closer to the user. As used herein, the terms "about" or "approximately" mean that the numerical value is approximate and small variations would not significantly affect the practice of the disclosed embodiments. As used herein, "tissue" refers both to soft tissue and to hard tissue, such as bone. As used herein, "laterally" means horizontally and either to the left or right, such that lateral directions are horizontal but transverse to a horizontal forward-backward axis.

Figure 1:
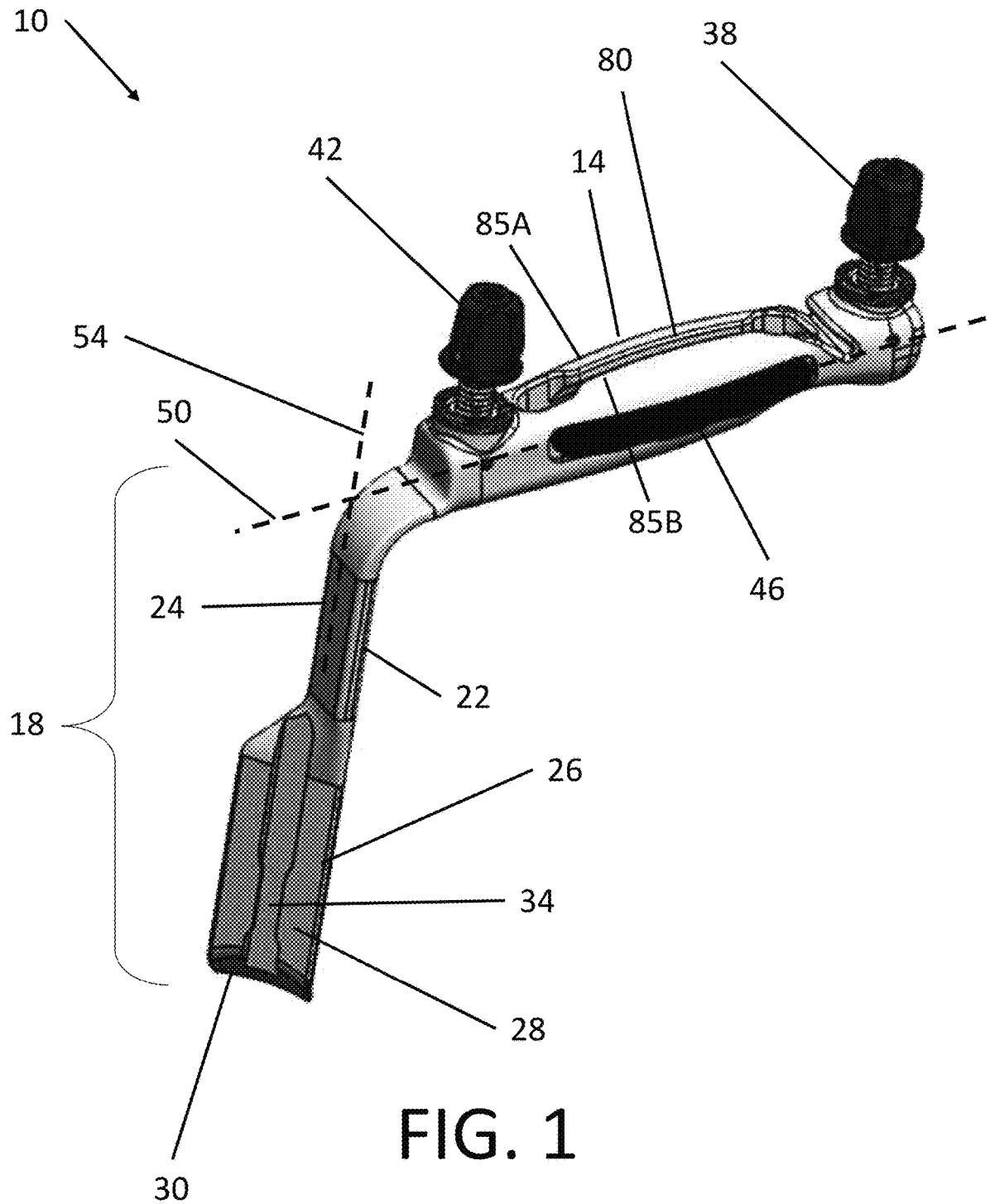
FIG. 1 is an oblique perspective view of a tissue retractor according to an embodiment of the disclosure.
Figure 2:
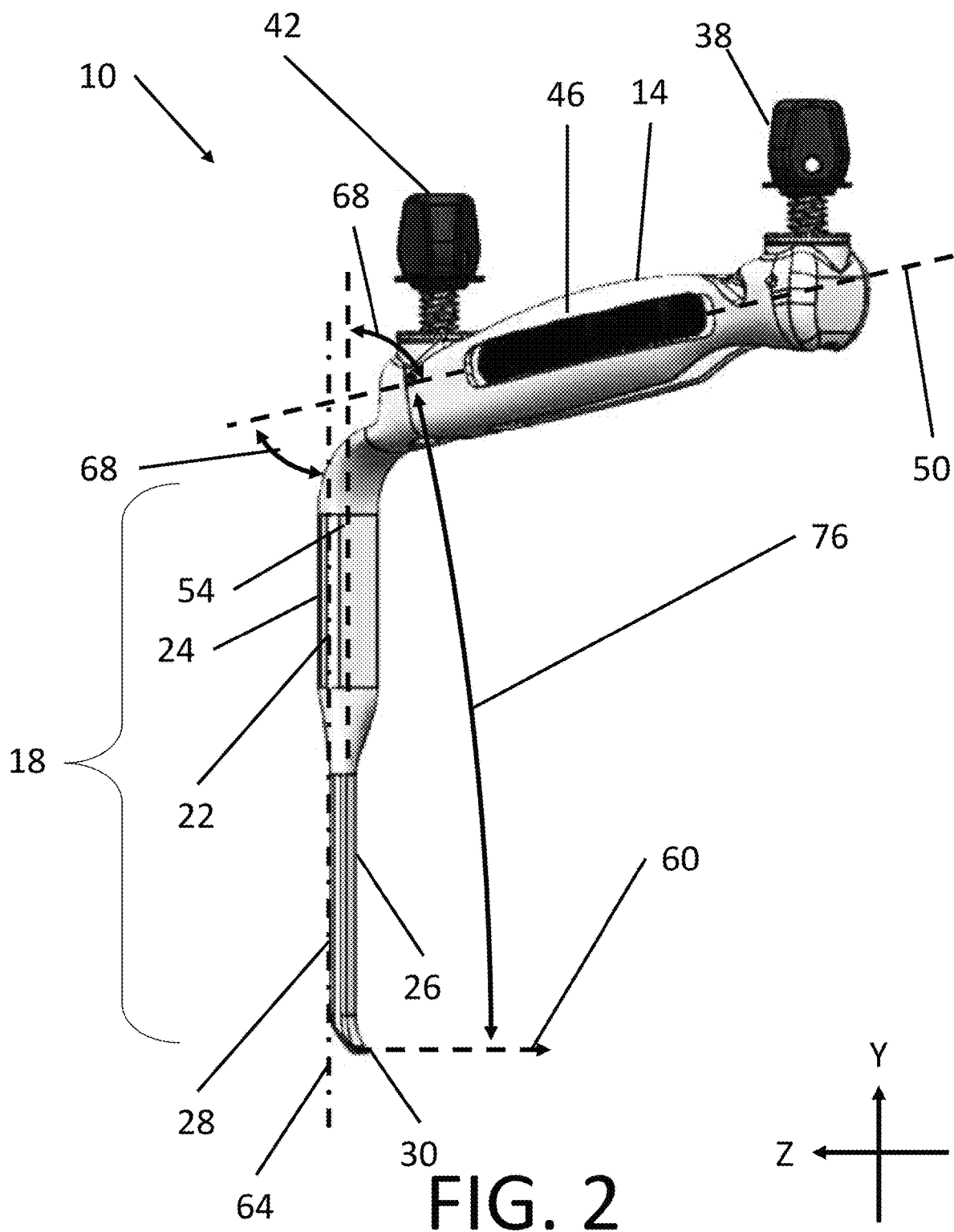
FIG. 2 is an elevation view of the tissue retractor of FIG. 1 on a plane perpendicular to a plane on which a front face of a distal portion of a blade of the retractor extends.
Figure 3:
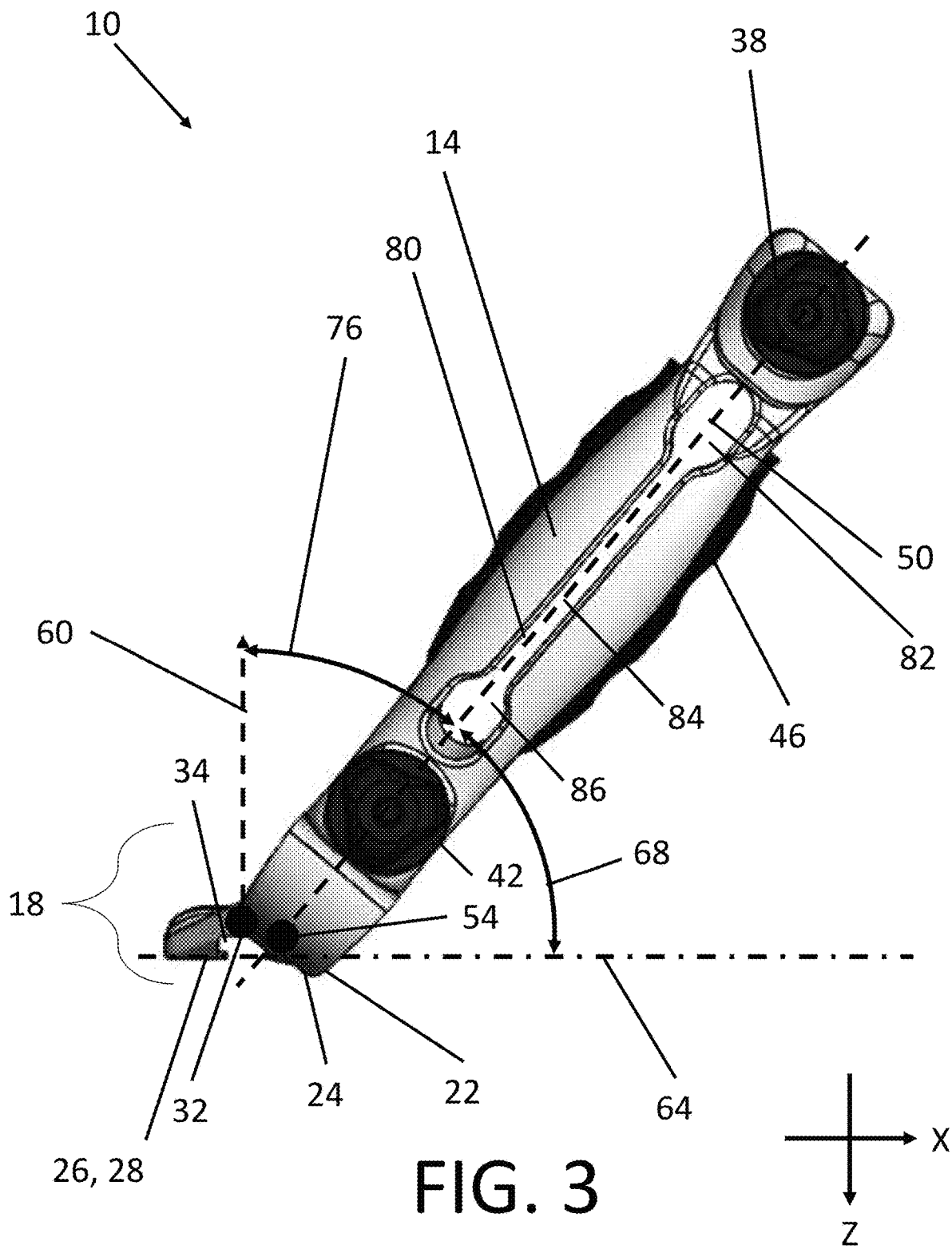
FIG. 3 is a top plan view of the tissue retractor of FIG. 1.

In a first aspect, the present disclosure relates to a retractor for use in surgery. One embodiment of a retractor is shown in FIGS. 1-3. Referring now to FIG. 1, a retractor for surgical use includes a handle 14 and a blade 18. In some non-limiting examples, the blade in this and other embodiments of the present disclosure may be made of titanium or stainless steel. Blade 18 further includes a proximal portion 22 and a distal portion 26. Proximal portion 22 extends between and connects handle 14 and distal portion 26. Distal portion 26 ends in a claw or back lip 30 that defines a distal end of distal portion 26. Back lip 30 curls back toward an end of distal portion 26 to create a small hook at the distal end of blade 18, as shown in FIG. 2. The direction in which back lip 30 curls defines the direction that blade 18 is best suited to pull tissue, as pulling retractor transversely to the curl of back lip 30 will increase the likelihood that back lip 30 will slide along the tissue's surface instead of engaging and pulling the tissue.

In the illustrated example, distal portion 26 of blade 18 is generally flat, planar, or plate-like in shape except for channel 34, discussed in greater detail below, and back lip 30, which curls toward a direction normal, or at least approximately normal, to a back surface of distal portion 26. "Normal" is used in the geometric sense herein. Thus, "normal" in this case refers to perpendicularity or orthogonality. The shape of at least the back surface of distal portion 26 also facilitates pulling tissue in the direction toward which back lip 30 curls by distributing force across contacted tissue in the same or about the same direction. In alternative arrangements, slightly curved blades 18 or blades 18 having flat or slightly curved back surfaces of distal portion 26 function similarly. Curved, round, pointed, or otherwise non-flat distal portions 26 are also contemplated. In some embodiments, the back lip 30 may be shallower or steeper than that shown in FIG. 1.

Retractor 10 is illustrated with a number of optional features. A channel 34 extends along a center of a front surface of distal portion 34. Channel 34 may be used, for example, to receive and guide surgical tools, lights, or endoscopes. A proximal connector 38 and a distal connector 42 provide attachment points by which retractor 10 may be connected to mechanical retracting assemblies, manual rigid arms to fix the retractor to a stationary point, or robotic arms. In some applications, such connectors may even provide points of leverage during manual use of retractor 10. Connectors 38, 42 in the illustrated example are threaded elements engaged within respective threaded bores extending into handle 14, though connectors of any other variety may be used in alternative arrangements. Ergonomic grips 46, which may be made of a more easily gripped or friction-conducive material than the rest of handle 14, such as rubber or textured metal, extend along either side of handle 14, though only one grip 46 is visible from the perspective of FIG. 1. These features along with certain others shown in FIG. 1 such as the back lip 30 discussed above may be omitted or reconfigured individually or in any combination in alternative arrangements. In some examples, back lip 30 may be omitted when retractor 10 may perform a required retraction without a curved lip at its tip.

Figure 4:
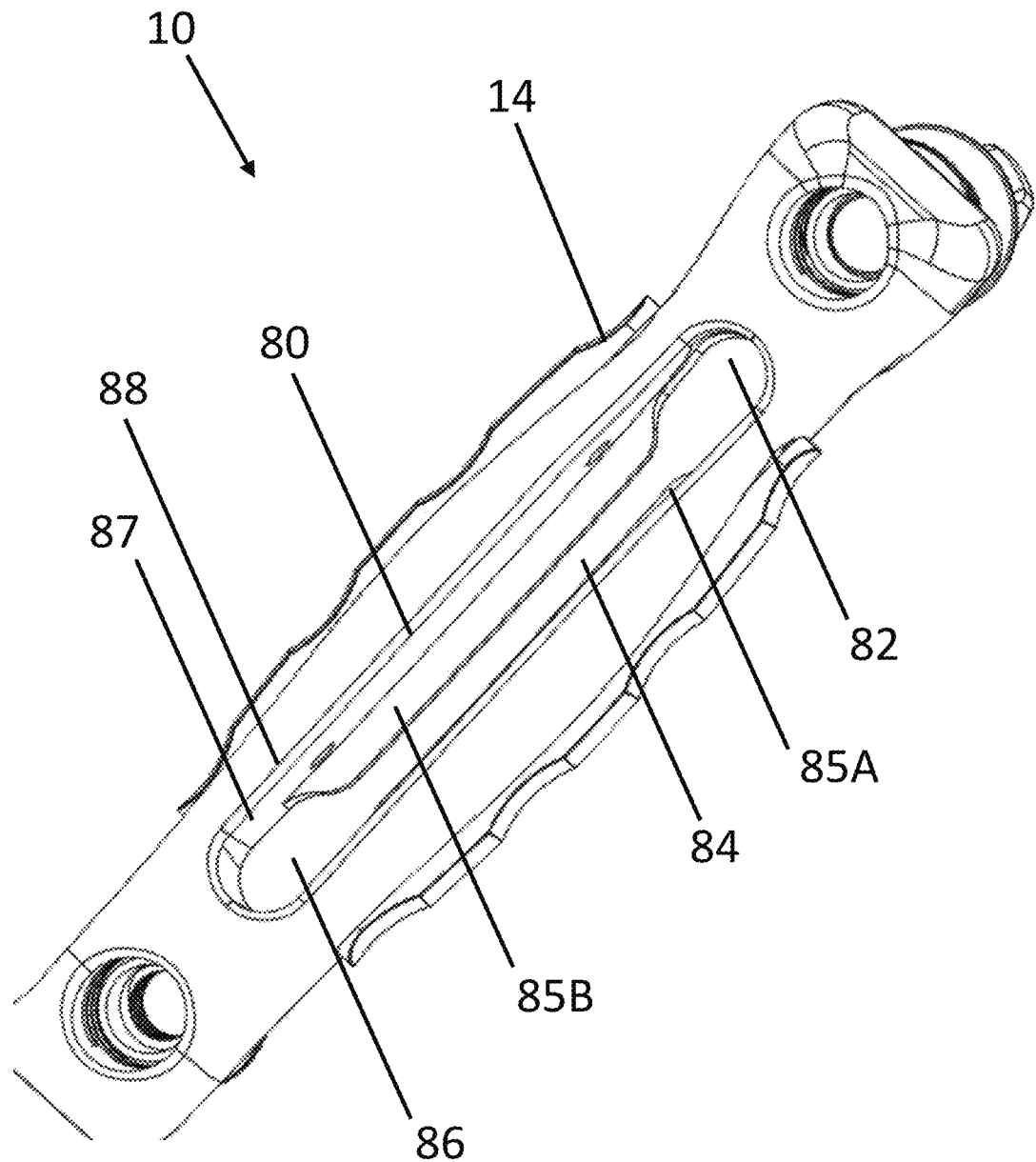
FIG. 4 is a partial perspective view of an underside of a handle of the tissue retractor of FIG. 1.

With continued reference to the handle, handle 14 also includes an elongate slot 80 that may be used to hold objects, such as cable, as described in greater detail elsewhere in the present disclosure. The slot 80 includes an enlarged proximal segment 82, central segment 84, and enlarged distal segment 86, as shown in FIG. 3, for example. Lateral ridges 85A, 85B protrude inward along a length of the central segment such that the central segment is narrower than enlarged proximal and distal segments 82, 86. Viewed from below, as shown in FIG. 4, lateral ridges 85A, 85B may be shallower than a depth of the handle such that lateral ridges 85A, 85B only protrude inward from an upper part of an enclosed internal wall 87 that defines an outer bound of slot 80. In this manner, an underside of slot 80 may have a generally uniform width along its length. In the depicted embodiment, a shape of the underside of slot 80 is defined by peripheral edge 88 with an elongate dimension having a uniform width and with semi-circular enclosures at ends in respective end segments 82, 86.

As shown in FIGS. 2 and 3, handle 14 extends along a handle axis 50. Handle axis 50 is laterally centered along handle 14 and in the illustrated example extends through the center points of the proximal and distal ends of the portion of handle 14 that is adapted to be gripped. Handle axis 50 may alternatively be defined to be collinear with the volumetric centerline of the portion of handle 14 intended to be gripped. In alternative arrangements wherein handle 14 is not adapted to be gripped by hand, handle axis 50 may be aligned along mechanical connectors 38, 42 if two connectors are present or, if only one mechanical connector 38, 42 exists, handle axis 50 may be aligned with the single connector and the point where blade 18 connects to handle 14. Relationships between other features and handle axis 50 described throughout this disclosure are intended to apply equally or in the alternative to any of the foregoing definitions of handle axis 50 unless specified otherwise. Handle 14 of the illustrated arrangement is straight such that handle axis 50 travels through, or at least near, a centerpoint of each cross-section of handle 14 on any plane normal to handle axis 50, each cross-section meaning any number of cross-sections measured at intervals along the length of the handle. In some arrangements, the handle itself may be non-linear over its length. In such cases, the handle axis will be defined by an overall alignment of the handle over its length accounting for all sub-sections. References to the handle axis elsewhere in the disclosure would refer to an axis established in such manner for these particular handle configurations.

Proximal portion 22 of blade 18 extends along a proximal blade axis 54 that is the volumetric centerline of proximal portion 22 excluding transitional structures at the proximal and distal ends of proximal portion 22 that connect proximal portion to handle 14 and distal portion 26, respectively. Proximal blade axis 54 is transverse to handle axis 50 by a handle-to-proximal blade angle 58. A front surface 24 of proximal portion 22 is shown in FIG. 1 and partially shown in FIG. 3. Handle to proximal blade angle 58 specifically refers to the true acute angle between handle axis 50 and proximal blade axis 54.

The term "acute angle" here refers to the narrower of the two angles formed between any two non-parallel lines or directionless axes in three-dimensional space, with the wider of the two angles being an obtuse angle equal to the absolute difference between 180° and the acute angle. However, reference to an acute angle is not intended to foreclose the possibility of two lines being perpendicular to each other in alternative arrangements. A "true" angle as used anywhere in the present disclosure refers to an angle that may be obtained by taking the inverse cosine of the dot product of two unit vectors, each of the unit vectors being along the respective lines or axes being compared. Thus, finding the "true acute angle" between any two axes or lines herein refers to selecting a unit vector along each of the compared axes such that the dot product between the selected unit vectors is positive. Similarly, the "true obtuse angle" between any two axes or lines herein refers to selecting a unit vector along each of the compared axes such that the dot product between the selected unit vectors is negative.

Handle-to-proximal blade angle 58 is therefore the narrowest angle defined by the intersection between handle axis 50 and proximal blade axis 54 on any plane of reference. It should be noted that handle-to-proximal blade angle 58 is projected onto the planes of FIG. 2, and therefore the appearance of handle-to-proximal blade angle 58 in FIG. 2 is somewhat distorted. That is, measurement of the angle between handle axis 50 and proximal blade axis 54 as projected onto the plane of FIG. 2 would not result in the true value of handle-to-proximal blade angle 58. Additionally, a proximal blade plane passes through front surface 24 of proximal portion 22. It should be appreciated that although proximal blade plane is defined in the applicable Figures and in certain arrangements as passing through the front surface of the proximal portion 22, it is contemplated that in some arrangements, the proximal blade plane may also pass through a width dimension of the proximal portion along an axis that bifurcates a body of the proximal portion and is generally parallel with the front surface. Handle axis 50 and proximal blade axis 54, to the extent such axis 54 is central along a length of the proximal portion 22, pass through a plane that is orthogonal to the proximal blade plane. This is because the proximal portion 22 and handle 14 of the retractor 10 are in alignment in such plane (referring to a plane into the page of FIG. 3 on axis 50 and normal to the proximal blade plane).

Distal portion 26 extends from proximal portion 22 and includes a front surface 28 that lies on a distal blade plane 64. A back surface of distal portion 26 may have one or more flat surfaces, or may have a convex shape. If the back surface of distal portion 26 is flat, the back surface may extend parallel to distal blade plane 86. If the back surface has multiple facets or is otherwise convex, distal blade plane 86 may be parallel to a tangent plane defined at a center or rearmost portion of the back surface of distal portion 26. As with the proximal portion, it should be appreciated that although distal blade plane is defined in the applicable Figures and in certain arrangements as passing through the front surface 28 of the distal portion 26, it is contemplated that in some arrangements, the distal blade plane may also pass through a width dimension of the distal portion along an axis that bifurcates a body of the distal portion and is generally parallel with the front surface. Due to the overall cross-sectional shape of the distal portion, even with varying configurations of the back surface, an overall orientation of the distal portion in the width direction would remain similar or the same as that of the front surface. Front surface 28 of distal portion 26 is skewed and laterally offset relative to front surface 24 of proximal portion 22. Front surface 28 of distal portion 26 may optionally also be skewed and laterally offset relative to handle axis 50 as shown in the example illustrated in FIG. 3. As shown through FIGS. 2 and 3, front surface 28 of distal portion 26 is in an X-Y plane, coincident with distal blade plane 64. The skew, or twist, between the distal portion 26 and the proximal portion 22 is evidenced by the fact that the front surface 24 of the proximal portion 22 passes through the X-Y plane and is at a non-zero angle with respect to it. As shown in FIGS. 1-3, the front surface 28 of distal portion 26 is at an angle of approximately 30 degrees relative to the front surface 24 of the proximal portion 22. In some arrangements, this angle may be any angle in a range from 5 degrees to 55 degrees. In some examples, the angle is in a range from 20 to 40 degrees. In some examples, the angle is in a range from 25 to 35 degrees. It should be appreciated that in arrangements where the handle 14 extends orthogonally, as measured in the X-Z plane, from a front surface 24 of the proximal portion 22, an angle between the front surface 28 of the distal portion 26 and a central axis 50 of the handle 14 is the angle between the proximal and distal front surfaces 24, 28, noted above, plus 90 degrees when measured in the same direction from the X-Y plane. Thus, if the angle between front surface 28 and front surface 24 is 30 degrees, then the angle between front surface 28 of distal portion and the central axis 50 of the handle 14 is 120 degrees.

As shown in FIGS. 1-3, distal portion 26 may have a length approximately equal to a length of the proximal portion 22 so that each portion represents about 50% of a length of blade 18. In some arrangements, the distal portion 26 may be any amount in a range from 30% to 70% of an overall length of blade 18. As shown in FIG. 2, distal portion 26 has a width greater than a width of proximal portion 22. Such relative dimensions of the blade 18 may be advantageous when employed in antero-lateral spinal access applications. In some arrangements, a width of the distal portion 26 is the same as the width of the proximal portion 22. In other arrangements, the width of the distal portion 26 is narrower than the width of the proximal portion 22.

An overall lengthwise direction that blade 18 extends from its point of connection to handle 14 in a vertical or Y direction. Distal blade plane 64 is therefore normal to certain axes that extend on a different horizontal trajectory than handle axis 50. Stated another way, a projection of handle axis 50 onto an X-Z plane as shown in FIG. 3 is not normal to distal blade plane 64. Moreover, no plane exists that contains both handle axis 50 and any axis normal to distal blade plane 64.

Distal blade plane 64 is illustrated as a dashed line in FIGS. 2 and 3 because the perspectives of FIGS. 2 and 3 are parallel to distal blade plane 64. Specifically, the perspective of FIG. 3 is along an X-axis, i.e., into the page, and the perspective of FIG. 3 is along the Y axis according to the coordinate system annotated on FIGS. 2 and 3. As stated above, distal blade plane 64 is an X-Y plane with no Z component. For this reason, distal blade plane 64 appears as a straight line in FIGS. 2 and 3.

Distal blade plane 64 is parallel to, but offset from, proximal blade axis 54 in the illustrated example, though in other arrangements, proximal blade axis 54 may lie on distal blade plane 64. Regardless, proximal blade axis 54 has no X or Z component, while handle axis 50 has at least an X and a Z component. Handle axis 50 may optionally also have a Y component as shown in the illustrated example. Because handle axis 50 includes an X and a Z component while proximal blade axis 54 has no X or Z component and distal blade plane 64 has no Z component, the plane on which handle axis 50 and proximal blade axis 54 lie is not normal to distal blade plane 64, but rather at an acute angle. Handle-to-distal blade angle 68, which is the true acute angle between handle axis 50 and distal blade plane 64, is therefore necessarily less than the handle-to-proximal blade angle 58. It should be noted that handle-to-distal blade angle 68 is projected onto the planes of FIGS. 2 and 3, and therefore the appearance of handle-to-distal blade angle 68 in FIGS. 2 and 3 is somewhat distorted. That is, measurement of the angle between handle axis 50 and distal blade plane 64 as projected onto the plane of FIG. 2 or FIG. 3 would not result in the true value of handle-to-distal blade angle 68.

Hook direction 60, which is the direction that back lip 30 points, is also shown in FIGS. 2 and 3. Hook direction 60 extends backward from back lip 30 along an axis that has no X component. The axis along which hook direction 60 extends may have a positive, negative, or zero Y component, according to various arrangements of retractor 10. Hook direction 60 is the direction that retractor 10 is best able to apply retracting force to tissue as pulling retractor 10 in hook direction 60 force the point of hook 60 directly into the retracted tissue rather than across the tissue's surface. In some arrangements, the hook direction is simply an axis normal to front surface 28 of distal portion 26. Because hook direction 60 is spaced from handle axis 50 along the Y axis at the location of blade 18 and has a different X-Z trajectory than handle axis 50, in that handle axis 50 has an X component while hook direction 60 does not, hook direction 60 neither runs parallel to handle axis 50 nor intersects handle axis 50 at any point. Moreover, no plane exists that contains both handle axis 50 and the axis along which hook direction 60 extends.

The non-parallel and non-intersecting relationship of hook direction 60 to handle axis 50 suits retractor 10 for different usage than typical preexisting Hohmann blades. Typical preexisting Hohmann blades have handles aligned over the engaging direction in which their distal point, blade, or other tissue engaging end is directed except that the handle may be inclined either up or down relative to said engaging direction. Typical preexisting Hohmann blades are therefore configured to best engage tissue when pulled straight backward or only slightly upward or downward relative to the length of the handle. Retractor 10, by contrast, is configured to best retract tissue at a skew angle 76 relative to handle axis, wherein skew angle 76 is the true acute angle between hook direction 60 and handle axis 50. As shown in FIG. 3, skew angle 76 extends laterally relative to handle axis 50. Retractor 10 therefore engages tissue best when pulled both back and to the side in contrast to preexisting Hohmann blades.

Turning specifically to FIG. 3, distal portion 26 is horizontally offset from proximal portion 22. That is, a central axis 54 of proximal portion is offset from a central axis 32 of distal portion. Distal portion 26 and central axis 32 of distal portion 26 may optionally also be laterally offset from handle axis 50. The projection of handle axis 50 onto a horizontal or X-Z plane as shown in FIG. 3 does not pass through a center of distal portion 26 as projected onto the same horizontal or X-Z plane. Retractor 10 during use will therefore contact tissue that to the side of the point where handle 14 transitions to blade 18 in contrast to preexisting Hohmann blades that typically contact tissue directly below the transition of handle 14 to blade 18.

In the illustrated example, if the projection of handle axis 50 onto the plane of FIG. 3 defines the forward-backward axis with blade 18 being at the forward end of handle 14, distal portion 26 is both offset to the right of handle 14 and is skewed to the right such that back lip 30, hook direction 60, and the back surface of distal portion 26 face a direction to the right of handle 14 on a first side of axis 54. In alternative arrangements, distal portion 26 may instead be offset and skewed to the left of handle 14, i.e., on a second side of axis 54 opposite the first side. In further arrangements, distal portion may be skewed to the left of handle 14 without any offset. In other alternative arrangements, distal portion 26 may be offset to the left of handle 14 while remaining skewed to the right. More generally, in various arrangements, distal portion 26 may be any combination of offset to the right, offset to the left, or horizontally centered on handle axis 50 and skewed to the left or right of handle 14.

Figure 7:
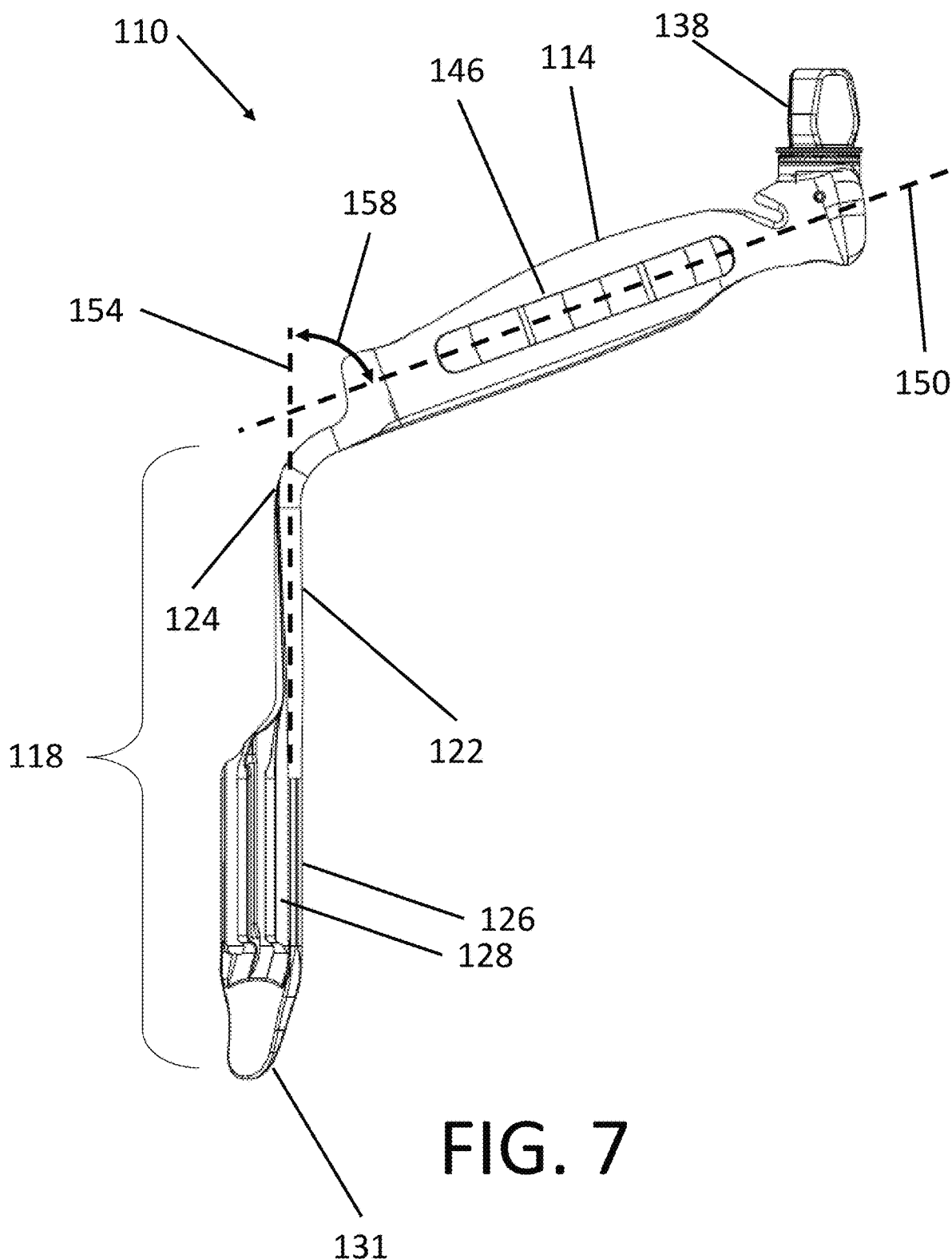
FIG. 7 is a side elevation view of a tissue retractor according to another embodiment of the disclosure.

Another embodiment of a retractor according to the first aspect is shown in FIG. 7. Retractor 110 is generally similar to retractor 10 shown in FIGS. 1-3 except for differences shown in FIG. 7 or specifically noted herein. Where numerals are indicated, reference numerals of the 100 series of numerals are the same as like numerals of the 10 series of numerals, unless otherwise indicated. Retractor 110 includes a handle 114 extending along a handle axis 150 with optional grips 146 on either side, a mechanical connection point 138 at a proximal or back end of handle 114, and a blade 118 extending downward or at least generally downward from a distal or forward end of handle 114. Blade 118 includes a proximal end 122 extending along a vertical proximal blade axis 154 and a distal portion 126 with a channel 134 running down a center of a front face of distal portion 126. The proportions, relative angles, properties, and possible variations of all of the foregoing features of retractor 110 of the illustrated example are identical to those illustrated and described above with regard to retractor 10 of FIGS. 1-3, except that no distal connector 42 exists on retractor 110 and retractor 110 includes an elongate tongue 131 instead of back lip 30.

The perspective of FIG. 7 is normal to both handle axis 150 and proximal blade axis 154. That is, both handle axis 150 and proximal blade axis 154 extend parallel to the plane on which FIG. 7 is illustrated. Handle-to-proximal blade angle 158 as visible in FIG. 7 is therefore equal to the true acute angle defined between handle axis 150 and proximal blade axis 154. Moreover, handle-to-proximal blade angle 158 of the illustrated example of retractor 110 may be the same as handle-to-proximal blade angle 58 of retractor 10 of FIGS. 1-3. In alternative arrangements, the angle between handle 114 and proximal portion 122 may vary from that shown.

In retractor 110, distal connector 42 is omitted while proximal connector 138 remains. In other arrangements of either retractor 10 or retractor 110, distal connector 42 may remain while proximal connector 38 or 138 is omitted. In further arrangements, more than two such connectors may be provided, or no connectors may be provided.

A front surface of distal portion 126 extends along a distal blade plane that is identical in orientation relative to other features of retractor 110 and in all other transferrable respects to distal blade plane 64 of retractor 10. Thus, a true acute angle between handle axis 150 and the distal blade plane of retractor 110 is equal to handle-to-distal blade angle 68 described above. A true acute angle between the plane of front surface 124 of proximal portion 122 and distal blade plane 164 is also the same as the angle between the plane of front surface 24 of proximal portion 22 and distal blade plane 64 as described above.

Tongue 131 extends mostly downward and slightly in a direction away from the distal blade plane on a side of the distal blade plane opposite the handle 114. Tongue 131 is thus laterally aligned both in direction with the distal portion 126. However, in contrast to back lip 30 which extended obliquely backward and somewhat horizontally toward handle 14, tongue 131 extends obliquely forward and somewhat horizontally away from handle 114. However, a shape of tongue 131 is adapted to optimize access and contact with anatomical surfaces and may be advantageous in circumstances different from those most suited to a retractor with back lip 30. It should be appreciated that either of the illustrated embodiments are well adapted for use in lateral and antero-lateral spinal procedures.

Figure 8:
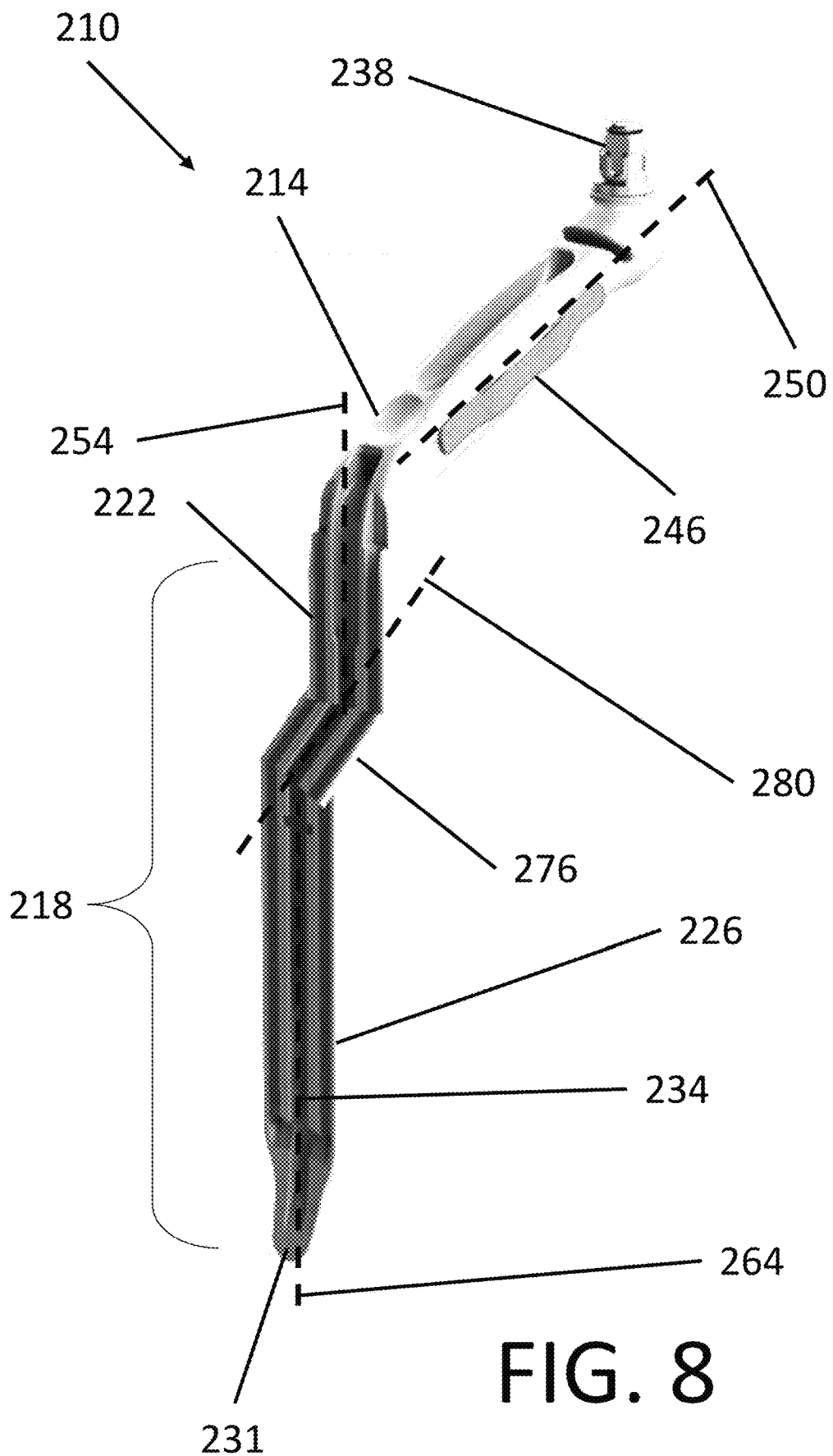
FIG. 8 is an oblique perspective view of a tissue retractor according to an embodiment of the disclosure.

Another embodiment of a retractor according to the first aspect, in the form of an offset retractor 210, is shown in FIG. 8. Where numerals are indicated, reference numerals of the 200 series of numerals are the same as like numerals of the 10 series of numerals, unless otherwise indicated. Offset retractor 210 of the illustrated arrangement includes many features generally similar to retractors 10, 110, including a handle 214 extending along a handle axis 250 with optional grips 246 on either side, a mechanical connection point 238 at a proximal or back end of handle 214, and a blade 218 extending downward or at least generally downward from a distal or forward end of handle 214. Blade 218 includes a proximal portion 222 extending along a vertical proximal blade axis 254 and a distal portion 226. A channel 234 is disposed along a center of a front face of proximal and distal portions 222, 226 and a tongue 231 extends downward and slightly forward from a distal end of distal portion 226.

Offset retractor 210 includes a middle portion 276 connecting proximal portion 222 to distal portion 226. Like distal portion 26 of retractor 10 and distal portion 126 of retractor 110, distal portion 226 of offset retractor 210 includes a back surface facing generally backward and under handle 214 that is, at its distal end at least, adapted to engage tissue. Middle portion 276 extends along a jog axis 280 that is transverse to both proximal blade axis 254 and a distal blade axis 264 along which distal portion 226 extends. Jog axis 280 extends laterally relative to proximal blade axis 254, distal blade axis 264. In this configuration, each axis 254, 264, 280 lie in a single plane. Distal portion 226 is offset laterally relative to proximal portion 222 on a first side of proximal blade axis 254. Distal portion 226 may be anywhere from half as long to twice as long as proximal portion 222 and anywhere from one third to two thirds of an overall length of blade 218. Middle portion 276 may be anywhere from one tenth to one third of an overall length of blade 218. According to various arrangements, the true acute angle between jog axis 280 and proximal blade axis 254 may be 45° anywhere from 30° to 60°, anywhere from 15° to 75°, or anywhere up to 90°. According to various arrangements, the true acute angle between distal blade axis 264 and proximal blade axis 254 may be 0°, as shown in the illustrated example, up to 30°, up to 60°, or anywhere up to 90°. In some examples, a distance between proximal axis 254 and distal axis 264 may be between 5 and 15% of a length of blade 218. In alternative arrangements, distal portion 226 may be offset laterally relative to proximal portion 222 on a second side of proximal blade axis 254, opposite to that shown in FIG. 8. In still further arrangements, distal portion 226 may be offset in a direction away from handle 214 such that a plane through the front face of distal portion 226 is further from the handle than a plane through the front face of proximal portion 222, such planes being spaced apart and parallel to one another.

Offset retractor 210 may therefore be used somewhat similarly to retractor 10 and retractor 110 such that handle 214 will be clear of space directly above tissue contacted by distal portion 226 to enable trajectories for an arm of a surgeon or other tools that would be obstructed if a conventional Hohmann blade 190 were used to pull the same tissue in the same direction. Unlike distal portion 26 and distal portion 126, distal portion 226 is not skewed or turned laterally relative to handle 214, meaning that the illustrated arrangement of offset retractor 210 is adapted to function best when pulled straight backward or slightly upward of straight backward, rather than when pulled at least partially laterally relative to handle 214. However, in alternative arrangements of retractor 210, distal portion 226 or at least a back, tissue engaging surface of distal portion 226 may be skewed laterally relative to handle 214 to be better suited to pull tissue laterally.

Figure 9:
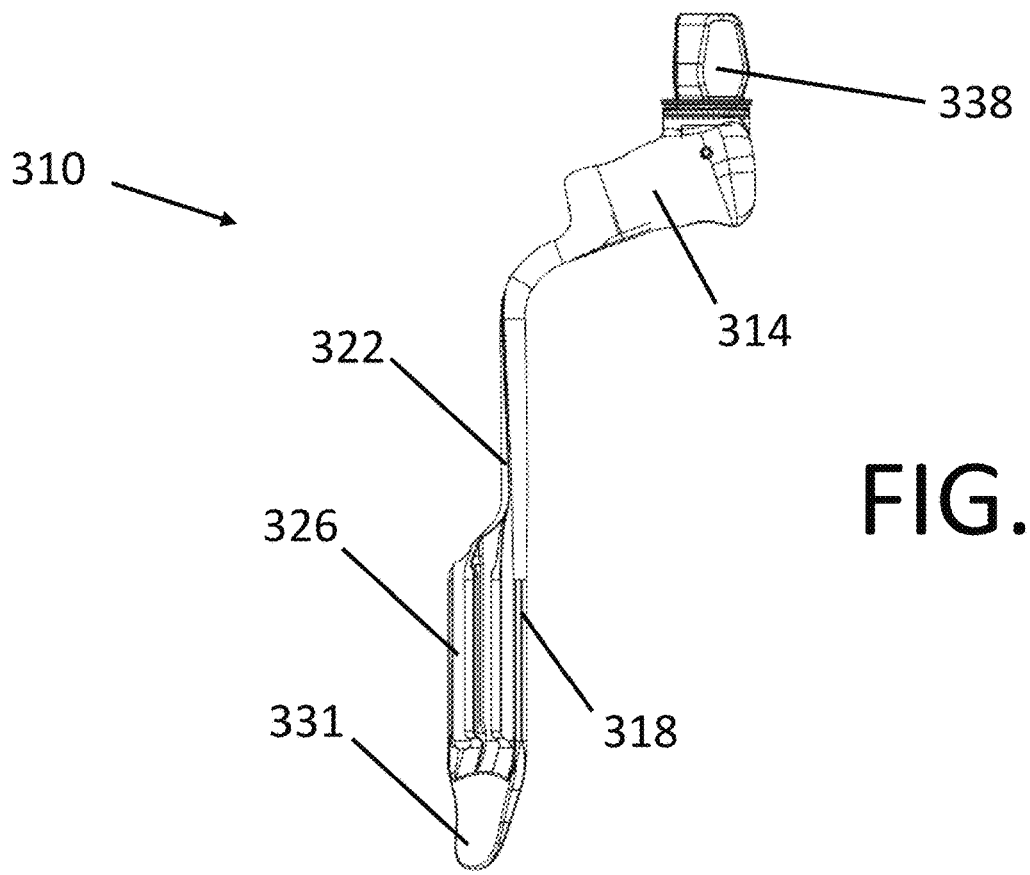
FIG. 9 is a side view of a tissue retractor according to an embodiment of the disclosure.

Further embodiments of the first aspect are shown in FIGS. 9, 10 and 11A-E, respectively. In FIG. 9, retractor 310 is shown. Where numerals are indicated, reference numerals of the 300 series of numerals are the same as like numerals of the 10 series of numerals, unless otherwise indicated. Retractor 310 includes a handle 314 and a blade 318 extending therefrom. The blade includes tongue 331 with a concave inner surface tapering in a direction away from a central longitudinal axis of the blade and away from a direction of the handle extending from the blade. Handle 314 is oriented transverse to a length of the blade and is short in length relative to the length of the blade. In one example, the length of the handle may be similar to a length of proximal portion 322 of blade 318. In other examples, the length of the handle may be shorter than a length of either proximal portion 322 or distal portion 326 of the blade. In still further examples, the length of the handle may be longer than the length of either the proximal portion or the distal portion. An upper surface of handle 314 may include a connector 338.

Figure 10:
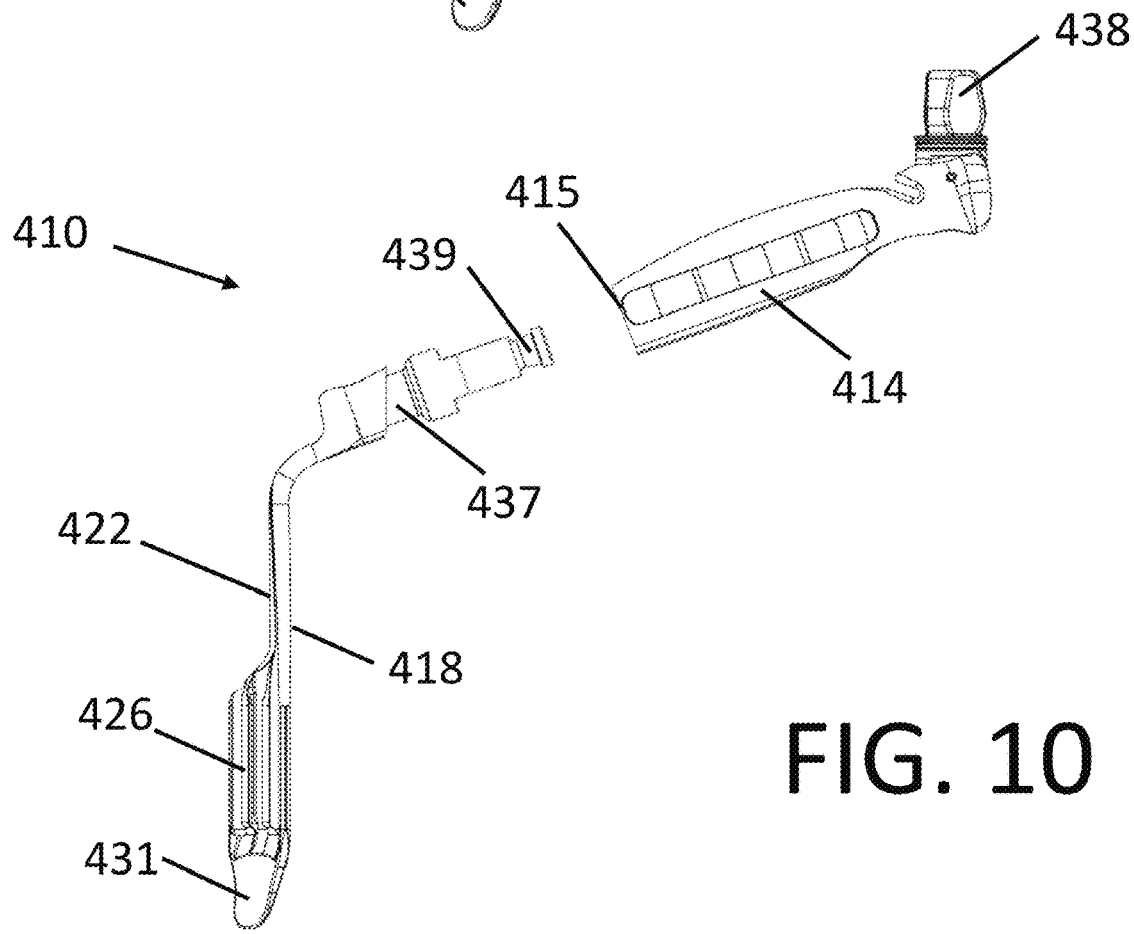
FIG. 10 is an exploded view of a tissue retractor according to an embodiment of the disclosure.

In FIG. 10, retractor 410 is shown. Where numerals are indicated, reference numerals of the 400 series of numerals are the same as like numerals of the 10 series of numerals, unless otherwise indicated. Retractor 410 includes a handle 414 and a blade 418 extending therefrom, where the blade is removably attached to the handle. In addition to the blade having proximal and distal portions 422, 426, the blade also includes a blade extension 437 extending proximally from proximal portion 422 and oriented transverse to an elongate dimension of the proximal portion. Blade extension 437 includes a free end defined by an engagement feature for engagement with the handle. The engagement feature may be positive or negative for engagement with a complementary feature on the handle. In the depicted embodiment, the engagement feature on blade extension 437 is an engagement head 439. With continued reference to the depicted embodiment, handle 414 includes an engagement portal 415 at one end for releasable engagement with engagement head 439 of the blade. While one particular set of engagement features is shown in FIG. 10, the details of the engagement features may vary from that shown.

Figure 11A:
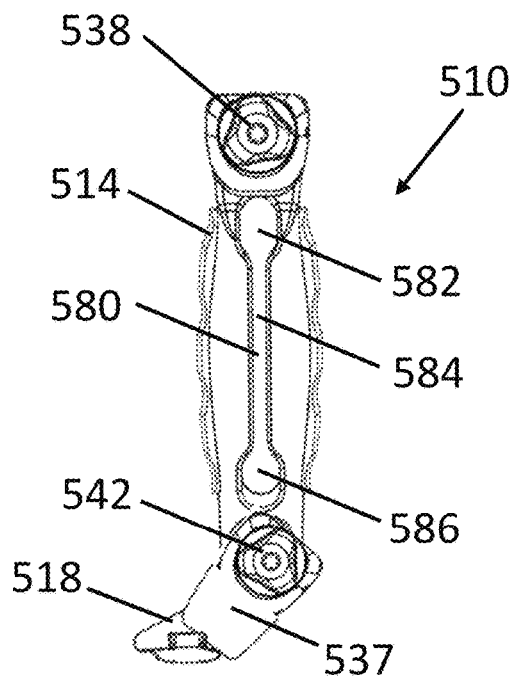
FIGS. 11A, 11B and 11C are top views of a retractor in different settings according to an embodiment of the disclosure.
Figure 11B:
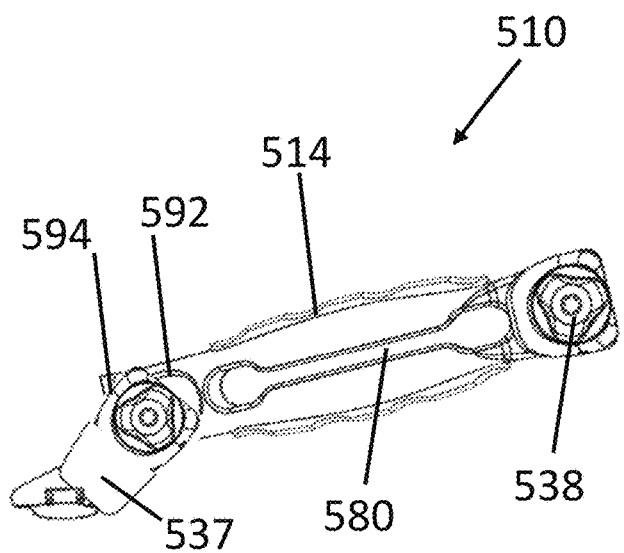
Figure 11C:
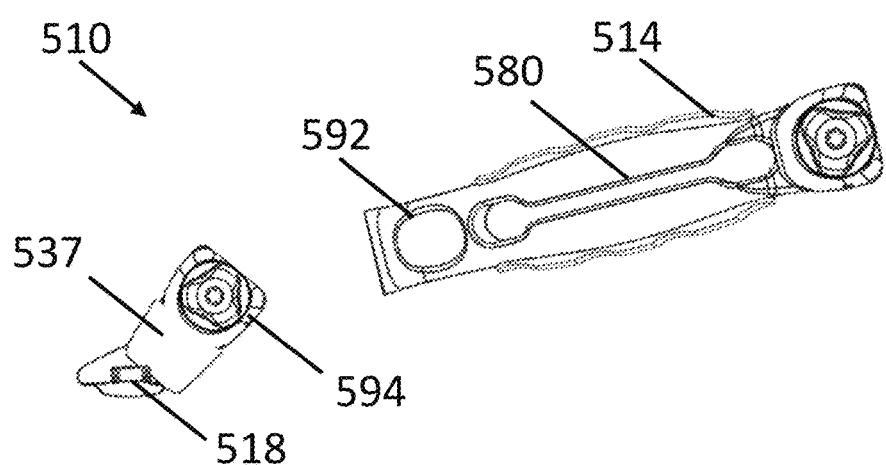

In FIGS. 11A-C, retractor 510 is shown. Where numerals are indicated, reference numerals of the 500 series of numerals are the same as like numerals of the 10 series of numerals, unless otherwise indicated. Retractor 510 includes a handle 514 and a blade 518 extending therefrom. Optionally, the blade may be removably attached to the handle. The retractor may include a blade extension 537 extending transversely from blade 518, and may further include a distal connector 542. Handle 514 may be attached to blade 518 in a manner such that handle 514 is pivotable relative to blade 518, as shown by the different positions of the handle relative to the blade in FIGS. 11A and 11B. Further, when the handle is rotatably adjusted relative to the blade, the new relative position of the components may remain set in place until force is applied to change them again. In this manner, the retractor may be used with a desired position of the handle relative to the blade. Thus, for example, retractor 510 may be used with the handle arranged as shown in FIG. 11A, with the handle arranged as shown in FIG. 11B, and in other positions in between, for example. The adjustable relationship between the handle and the blade may be such that the handle is continuously adjustable relative to the blade based on the force applied to the rotation of the handle relative to a held-in-place blade. Alternatively, the retractor may include an interface between the handle and the blade that facilitates adjustment of the handle relative to the blade in predetermined increments.

In examples with a continuously adjustable interface between the handle and blade, the retractor may include a friction-based interface between the handle and the blade with properties such that the resistance between the two may be overcome with force. In such arrangements, once force is no longer applied, the relative position between the handle and blade may remain static and will not change unless rotational force is applied again.

In examples where the interface supports adjustment of the handle relative to the blade in predetermined increments, one or a combination of a rotatable engagement region 592 on the handle and a rotatable engagement region 594 on the blade extension may include a gear and a pawl adapted such that the handle may be rotated in predefined increments in either a clockwise or counterclockwise direction. One non-limiting example of a mechanism that performs such a function is described in U.S. Pat. No. 6,116,580, the disclosure of which is hereby incorporated by reference herein in its entirety. Other arrangements with gears and other mechanical parts may also be used and are also contemplated for inclusion in the interface.

Figure 11D:
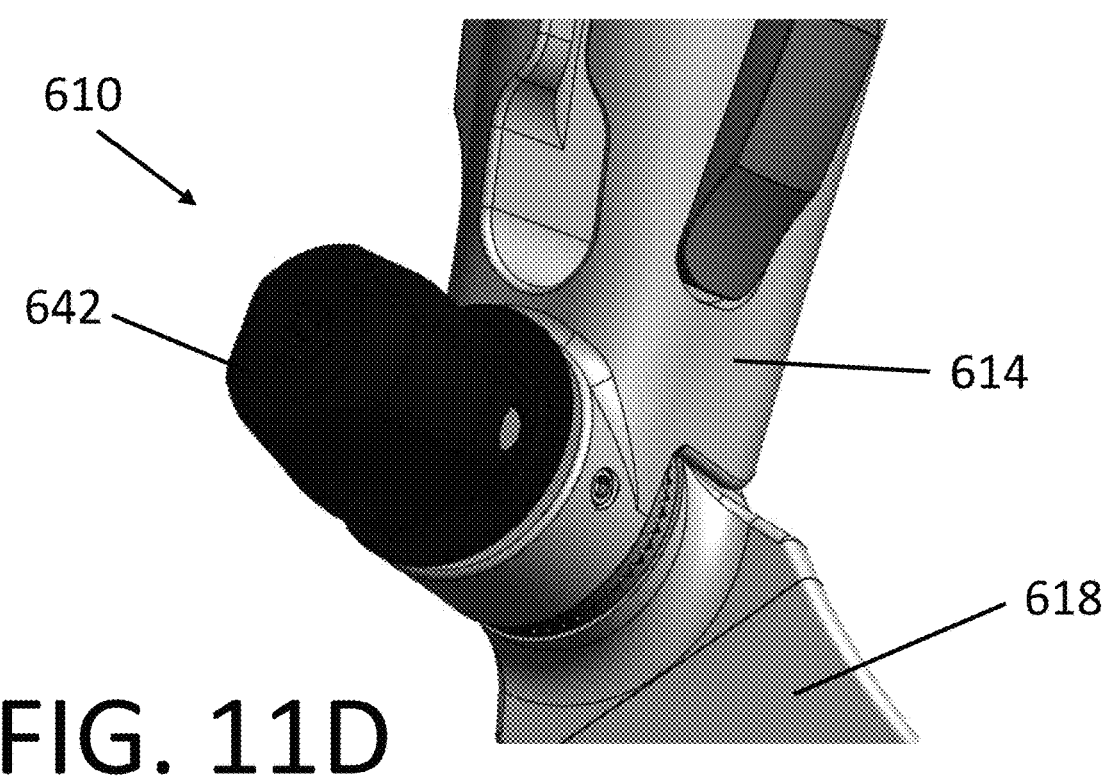
FIGS. 11D and 11E are partial perspective views of a retractor in different settings according to an embodiment of the disclosure.
Figure 11E:
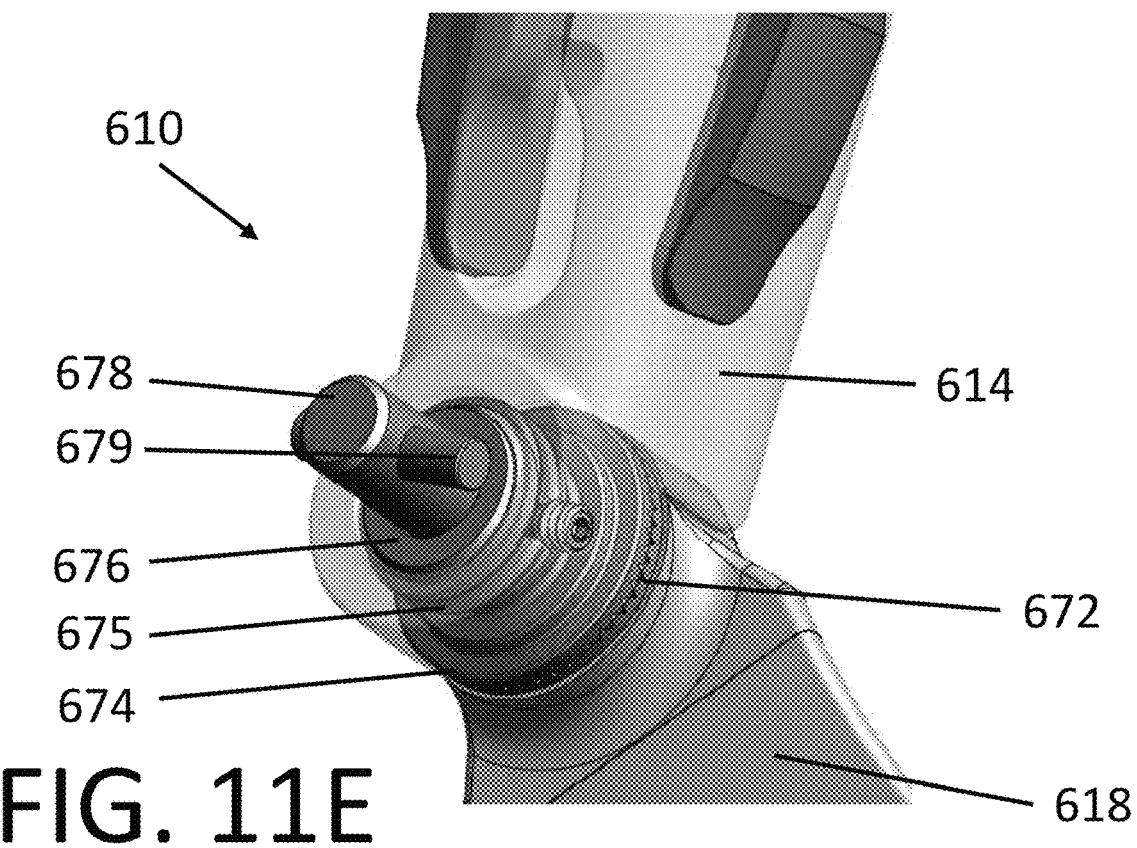

Another example of an interface adjustable in predetermined increments is that included in retractor 610 shown in FIGS. 11D and 11E. Where numerals are indicated, reference numerals of the 600 series of numerals are the same as like numerals of the 10 series of numerals, unless otherwise indicated. Although only a portion of the retractor is depicted in FIGS. 11D and 11E, it should be appreciated that such retractor may include a twist or skew in a distal portion of the blade relative to a proximal portion of the blade, as described in other embodiments of the present disclosure. A connection assembly may include a pin 678, a knob anchor 679 and an insert 676, in addition to handle 614 and blade 618. A rotatable engagement region of the handle includes a cylindrically shaped opening to receive insert 676 and pin 678. Insert 676 may include a threaded outer surface 675 for engagement with a complementary thread on an inner surface of the cylindrically shaped opening of the handle. In some examples, insert 676 may be pre-attached to the handle through the threaded connection. A small transversely oriented pin may be disposed through the handle onto the insert for increased engagement between the components. Further, the insert may include a hirth joint 674 at a blade-facing end oriented to be received on a complementary hirth joint 672 on the blade and may have an elongate opening therethrough sized for disposal of pin 678 therein. Pin 678 may include a transverse opening to receive knob anchor 679, as shown in FIG. 11E and may be threaded at one end for securement to the blade. Materials used for the connection assembly may be one or more of steel, stainless steel, aluminum and titanium.

The connection assembly is configured for use as follows. In one example, a starting condition may have a threaded end (not shown) of pin 678 rotatably engaged with a complementary thread on an inner receiving surface (not shown) of blade 618. Other forms of engagement may also be used. On handle 614, insert 676 may be rotatably engaged to the inner threaded surface of the cylindrically shaped opening of the handle. With knob anchor 679 removed from pin 678, the cylindrically shaped opening of the handle may be placed over pin 678 so that the inner wall of insert 676 slides over pin 678 and the respective hirth joints 672, 674 may be engaged such that a desired angle between handle 614 and blade 618 is realized. Knob anchor 679 may then be slid through pin 678 as shown in FIG. 11E, and knob 642 may be secured into place over pin 678. When knob 642 is secured in place, a rotational position of handle 614 relative to blade 618 is set until the knob is removed. The handle may be secured in different positions relative to the blade by engaging the respective hirth joints at different positions with respect to each other.

In variations where the blade is removably attached to the handle, rotatable attachment region 592 of handle 514 may include an engagement feature that is either a projection or a receiving portal and rotatable attachment region 594 of blade extension 537 may include the other of a projection or a receiving portal to complement the feature on the handle. In this way, the handle may be detached and reattached to the blade. In some examples, the engagement features on the handle and blade extension may be oriented along a longitudinal axis of the handle. In other examples, the engagement feature of the blade extension may be on an underside surface of blade extension 537 opposite distal connector 542 and the engagement feature on the handle may be oriented to complement the engagement feature on the blade extension. In these examples, a central axis through the respective engagement features may be parallel to a longitudinal axis of blade 518, passing through distal connector 542.

In another aspect, a kit is contemplated that may include one or more Hohmann blade as described in the present disclosure. For example, a kit may include one or more blades 10 and one or more blades 110. In other embodiments, a kit may include one or more Hohmann blades and a retractor frame, rigid arm, or both. In some embodiments, a kit may include any number of Hohmann blades and a manual with directions on the use of one or more items included in the kit. Optionally, such kits may also include one or both of a retractor frame and a rigid arm to hold the Hohmann blade.

In any one of the above embodiments, the kit or individual items and combinations thereof may be disposed within a packaging or a plurality of packages. It is contemplated that the items of a given kit may be sorted into any subgroups desired, where each subgroup may be packaged separately. Of course, each item of a kit may also be individually packaged. For example, each Hohmann blade in a kit may be packaged separately. Through packaging each item in the kit separately or in separate combinations, sterility may be controlled for each item within the kit.

In yet another aspect, a system that includes a Hohmann blade is contemplated. In one embodiment, a system includes a rigid arm with a connector at an attachment end and a Hohmann blade with a connector to receive the connector of the rigid arm. In another embodiment, a system includes a retractor frame with a connector and a Hohmann blade, where the Hohmann blade has a connector that receives the connector on the retractor frame. It is contemplated that the embodiments of the system may include any Hohmann blade contemplated by the present disclosure.

In another aspect, the present disclosure relates to a method of using a retractor such as those shown in FIGS. 1-11E. In one embodiment, a retractor, such as retractor 10, 110, 210, is used as part of a procedure to create access to a spine, such as from an antero-lateral access direction. Specifically, this may be done to prepare for an anterior lumber interbody fusion. In some examples, this procedure may be performed in the L5-S1 space. In such a procedure, the retractor, i.e., Hohmann blade, may be used to remove vessels away from a spinal disc space. With the blades contemplated by the present disclosure, the skew and offset of the blade allow for the blade to be held in place to pull vessels out of the target site, here, the intervertebral disc space, while still allowing space at the same time for an instrument or an arm of a surgeon to be inserted to access the same disc space. These principles may also be applied in other surgical settings where blood vessels or other tissue is intended to be retracted, while additional instruments must be inserted in the vicinity of the Hohmann blade once the Hohmann blade is in place and the tissue is retracted. Accordingly, one advantage of the present disclosure is that the contemplated Hohmann blade reduces the need to move or adjust a position of the blade during surgery. Additionally, because there is a reduced need to move the blade, risk of vascular injury due to such movement is reduced.

Figure 12A:
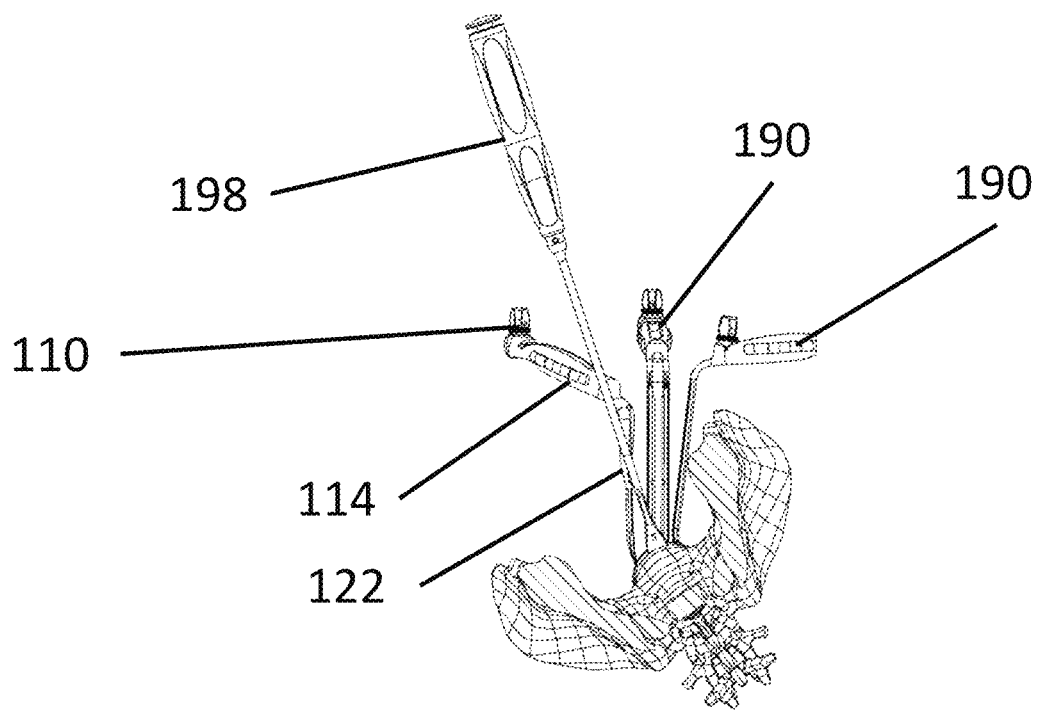
FIG. 12A is an end view of a retraction achieved with the retractor of FIG. 7 in one step of an embodiment of a method of the disclosure.
Figure 12B:
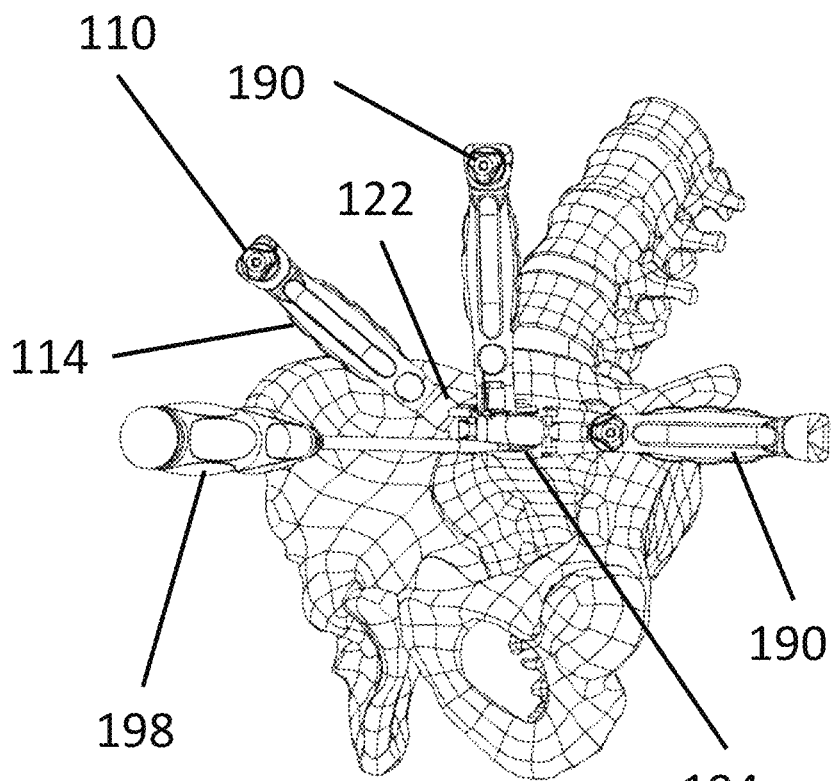
FIG. 12B is a plan view of the retraction shown in FIG. 12A.

One example of a Hohmann blade retractor used during a surgical method is shown in FIGS. 12A and 12B and utilizes retractor 110. Retractor 110 is used in cooperation with two conventional Hohmann blades 190 to retract tissue and hold open an opening 194. Specifically, with reference to the perspective of FIG. 12B, Hohmann blades 190 are used to pull tissue laterally and anteriorly and retractor 110 is used to pull tissue laterally in a direction opposite to opposing blade 190. Retractor 10, 110 may be pulled so that distal portion 26, 126 of blade 18, 118 moves along axis 60. In some examples, retractor 10, 110 may be pulled so that the distal portion moves along a direction that is at an angle relative to the axis 60. For instance, retractor 10, 110 may be pulled so that the distal portion moves in a direction five, ten, fifteen or twenty degrees off of axis 60. Advantageously, because blade handle and proximal portion of blade 110 are skewed relative to distal portion retracting tissue, extra space is provided for placement of cobb tool 198, as shown in FIG. 12B. In particular, tool 198 can be advanced into opening 194 directly from the lateral side shared with retractor 110 according to the perspective of FIG. 12B. More generally, reference to both FIGS. 12A and 12B show that tool 198 can extend through a space that would be obstructed by a conventional Hohmann blade 190 if a conventional Hohmann blade 190 were used instead of retractor 110 pull the same tissue in the same direction. The procedure and arrangement of devices 110, 190, 198 of FIGS. 12A and 12B is merely one example, and it is contemplated that a wide variety of potential use cases exist wherein a useful trajectory for any type of tool may be cleared by using a retractor 110 that is either or both of offset and skewed instead of a conventional Hohmann blade 190. Retractor 110 may also be used simply for convenience or ergonomic purposes where manually pulling tissue in an intended direction would be inconvenient with a conventional Hohmann blade 190. Retractor 10, offset retractor 210, or retractors 310, 410, 510 may be used in generally similar ways to the manner of use of retractor 110 as illustrated in FIGS. 12A and 12B and described herein with respect thereto.

In another aspect, the present disclosure relates to cable management for retractors. Generally, this means keeping cables that are placed in and around a surgical access portal out of the way of the working space so that the working space remains unobstructed. Surface features on a handle of the retractor are shaped to receive and hold cable, thereby keeping such cable out of the way of the access portal and/or other areas, as needed. It should be appreciated that the cable contemplated for use with the retractors of the present disclosure may be light cable or other types of cable typically placed into a surgical field. Other types of cable that may be used may be of a size similar in scale to light cable.

Figure 5:
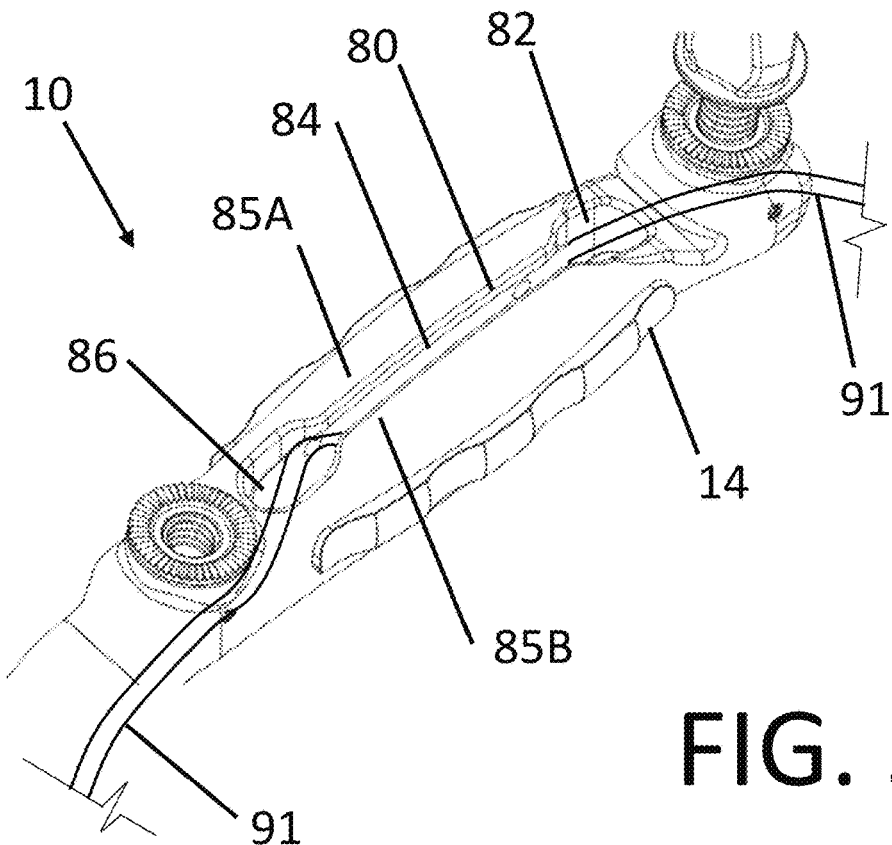
FIG. 5 is a partial perspective view of the tissue retractor of FIG. 1 with a cable disposed therein.

In one embodiment, cable management is facilitated through slot 80 in handle 14 of retractor 10, as shown in FIG. 5. Retractor 10, partially depicted in FIG. 5, is also shown in FIGS. 1-4. From its source, cable 91 may be first disposed into enlarged proximal segment 82 of slot 80, then run through or under lateral ridges 85A, 85B within the slot before exiting from the slot through enlarged distal segment 86. Passing the cable through the slot holds a portion of the cable in place on the handle and prevents it from drifting away from its location in the handle. In other exemplary applications, cable 91 may simply be pressed into slot 80 by pressing the cable in along central segment 84. If desired, cable 91, already positioned within slot 80, may be run through an engagement surface on a blade of the retractor, in between walls defining channel 34, for example. In such arrangements, an end of the cable 91 (not shown) may be positioned on the blade. The cable used may be any type of cable, such as light cable. Where light cable is used, a light emitting diode ("LED") may be positioned on a free distal end of the cable so that when it is positioned on the blade, light may emanate from the blade.

Figure 6:
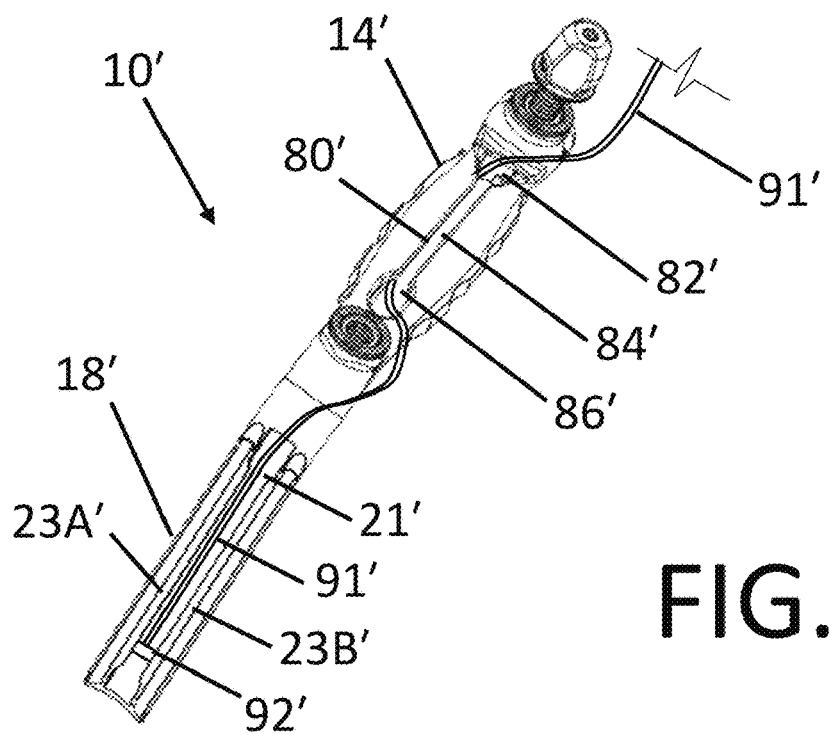
FIG. 6 is a perspective view of a retractor with a cable disposed therein according to an embodiment of the disclosure.

In another embodiment, cable management is facilitated through slot $80'$ in handle $14^1$ of retractor $10^1$, as shown in FIG. 6. In retractor $10^1$, like reference numerals refer to like elements of retractor 10, unless otherwise indicated. For the avoidance of ambiguity, slot $80^1$ may be the same as slot 80. When cable $91^1$ is passed through or pressed into slot $80^1$, it may then be further directed through an elongate channel $21^1$ in blade $18^1$, as shown in FIG. 6. Channel 21 may be defined by a space between elongate ridges $23A^1$, $23B^1$ on the blade. Cable $91^1$ as shown is a light cable with an LED $92^1$ at its distal end. If desired, a free end of cable $91^1$ may be run through channel $21^1$ until the LED $92^1$ is at a desired position for use on blade $18^1$.

Although the concepts herein have been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

The invention claimed is:

1. A surgical retractor tool comprising:
a handle; and
a blade extending from an end of the handle, the blade having a length extending from a proximal end of a proximal portion of the blade to a distal end of a distal portion of the blade, the proximal portion having first and second lateral edges and the distal portion including a proximal subportion and a distal subportion, the distal subportion having third and fourth lateral edges,
wherein the proximal portion has a first central longitudinal axis and the distal subportion has a second central longitudinal axis parallel to the first central longitudinal axis,
wherein the first and second lateral edges are coincident with a first plane and the third and fourth lateral edges are coincident with a second plane, the first plane being transverse to the second plane,
wherein the first plane and the second plane are both orthogonal to a third plane,
wherein a first front surface in the proximal subportion of the distal portion extends from the proximal portion toward the distal subportion such that an edge of the first front surface flares outward from the proximal portion toward one of the third or fourth lateral edges, and wherein an entirety of a second front surface extending from the third lateral edge to the fourth lateral edge is oriented at a non-zero angle relative to the first plane.

2. The surgical retractor tool of claim 1, wherein the second lateral edge and the fourth lateral edge are coincident with a first linear axis.

3. The surgical retractor tool of claim 1, wherein the blade includes a tongue that defines a distalmost portion of the distal portion, the tongue curving into a first side of the second plane opposite a second side of the second plane, the handle being on the second side.

4. The surgical retractor tool of claim 3, wherein a surface of the tongue facing away from the second side is concave and a tip of the tongue is curved.

5. The surgical retractor tool of claim 1, wherein the distal portion is partially on and extends from one side of the first plane.

6. The surgical retractor tool of claim 1, wherein a central longitudinal axis of the handle is at an angle relative to the first plane.

7. The surgical retractor tool of claim 1, wherein a minimum distance between the first and second lateral edges is less than a minimum distance between the third and fourth lateral edges.

8. The surgical retractor tool of claim 7, wherein the first front surface of the proximal subportion includes a concave surface and a convex surface, the first front surface of the proximal subportion being opposite a tissue contacting surface of the proximal subportion.

9. The surgical retractor tool of claim 1, wherein the handle includes an elongate slot enclosed within a length of the handle, the elongate slot extending at least partially into the handle and having opposite ends with a wider dimension than a central segment in between the opposite ends.

10. The surgical retractor tool of claim 1, wherein the distal portion is skewed relative to the proximal portion such that an angle between the first plane and the second plane is in a range from 5 to 55 degrees.

11. A surgical retractor tool, comprising:
a handle adapted for holding the retractor tool; and
a blade extending from a front end of the handle at a non-zero angle relative to the handle, the blade comprising a proximal portion and a distal portion, the distal portion having a first width measured along a first front surface of the distal portion and the proximal portion having a second width measured along a second front surface of the proximal portion, an entirety of the first front surface being skewed relative to the second front surface, and the first width being greater than the second width.

12. The surgical retractor tool of claim 11, wherein the second front surface of the proximal portion passes through a first plane and the first front surface of the distal portion passes through a second plane, the second plane crossing the first plane along an axis through a length of the blade.

13. The surgical retractor tool of claim 12, wherein the blade further comprises a distal end with a tapered tip curving out of the second plane such that the tapered tip and the handle extend from the same side of the second plane.

14. The surgical retractor tool of claim 12, wherein the blade further comprises a distal end with a tapered tip curving out of the second plane such that the tapered tip is on a first side of the second plane and the handle is on a second side of the second plane.

15. The surgical retractor tool of claim 11, wherein the distal portion has a first central longitudinal axis and the proximal portion has a second central longitudinal axis, the first central longitudinal axis being laterally offset from the second central longitudinal axis.

16. The surgical retractor tool of claim 11, wherein the distal portion is skewed relative to the proximal portion such that an angle between a first plane through lateral sides of the first front surface and a second plane through lateral sides of the second front surface is in a range from 25 to 35 degrees.

* * * * *